United States Patent
Han

(10) Patent No.: US 10,092,197 B2
(45) Date of Patent: Oct. 9, 2018

(54) REFLECTIVE SURFACES FOR PPG SIGNAL DETECTION

(71) Applicant: Apple Inc., Cupertino, CA (US)

(72) Inventor: Chin San Han, Mountain View, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 14/470,834

(22) Filed: Aug. 27, 2014

(65) Prior Publication Data

US 2016/0058309 A1    Mar. 3, 2016

(51) Int. Cl.
| | |
|---|---|
| A61B 5/00 | (2006.01) |
| A61B 5/024 | (2006.01) |
| A61B 5/026 | (2006.01) |
| A61B 5/0295 | (2006.01) |
| A61B 5/1455 | (2006.01) |

(52) U.S. Cl.
CPC ........ *A61B 5/02427* (2013.01); *A61B 5/0013* (2013.01); *A61B 5/0261* (2013.01); *A61B 5/0295* (2013.01); *A61B 5/02438* (2013.01); *A61B 5/14551* (2013.01); *A61B 5/681* (2013.01); *A61B 5/6898* (2013.01); *A61B 5/7264* (2013.01); *A61B 2562/0233* (2013.01)

(58) Field of Classification Search
None
See application file for complete search history.

(56) References Cited

U.S. PATENT DOCUMENTS

| 5,483,261 A | 1/1996 | Yasutake |
| 5,488,204 A | 1/1996 | Mead et al. |
| | (Continued) | |

FOREIGN PATENT DOCUMENTS

| JP | 2000-163031 A | 6/2000 |
| JP | 2002-342033 A | 11/2002 |
| | (Continued) | |

OTHER PUBLICATIONS

International Search Report dated Nov. 6, 2015, for PCT Application No. PCT/US2015/042982, filed Jul. 30, 2015, five pages.

(Continued)

*Primary Examiner* — Tse Chen
*Assistant Examiner* — Joanne Hoffman
(74) *Attorney, Agent, or Firm* — Morrison & Foerster LLP

(57) ABSTRACT

Reflective surfaces for the apertures of PPG optical components in PPG systems is disclosed. In a PPG system or device, the addition of reflective surfaces around, under, or near the apertures of the optical components can enhance the amount of light received by the light detector. As a result, the measured PPG signal strength can be higher and more accurate compared to the same PPG device without reflective surfaces. The reflective surfaces can reflect and/or recycle light that is incident upon the reflective surfaces back into the skin for eventual capture of the light by the light detectors. In some examples, the reflective surfaces can be diffuse or specular reflectors and/or can be configured to selectively reflect one or more wavelengths of light. In some examples, the back crystal and/or component mounting plane of the PPG system can be made of the same material as the reflective surfaces.

19 Claims, 23 Drawing Sheets

(56) References Cited

U.S. PATENT DOCUMENTS

| | | | |
|---|---|---|---|
| 5,759,156 A * | 6/1998 | Hayakawa | A61B 5/02438 600/483 |
| 5,825,352 A | 10/1998 | Bisset et al. | |
| 5,835,079 A | 11/1998 | Shieh | |
| 5,880,411 A | 3/1999 | Gillespie et al. | |
| 6,188,391 B1 | 2/2001 | Seely et al. | |
| 6,277,067 B1 * | 8/2001 | Blair | A61B 1/00041 348/77 |
| 6,310,610 B1 | 10/2001 | Beaton et al. | |
| 6,323,846 B1 | 11/2001 | Westerman et al. | |
| 6,533,729 B1 * | 3/2003 | Khair | A61B 5/021 600/480 |
| 6,690,387 B2 | 2/2004 | Zimmerman et al. | |
| 7,015,894 B2 | 3/2006 | Morohoshi | |
| 7,139,076 B1 * | 11/2006 | Marbach | G01N 21/474 356/446 |
| 7,184,064 B2 | 2/2007 | Zimmerman et al. | |
| 7,450,799 B2 | 11/2008 | Selbrede et al. | |
| 7,616,110 B2 | 11/2009 | Crump et al. | |
| 7,643,153 B2 * | 1/2010 | de Boer | A61B 5/0059 356/479 |
| 7,663,607 B2 | 2/2010 | Hotelling et al. | |
| 7,729,748 B2 | 6/2010 | Florian | |
| 8,252,369 B2 | 8/2012 | Jiang | |
| 8,378,811 B2 * | 2/2013 | Crump | A61B 5/02055 128/903 |
| 8,479,122 B2 | 7/2013 | Hotelling et al. | |
| 8,618,930 B2 | 12/2013 | Papadopoulos et al. | |
| 2002/0151775 A1 * | 10/2002 | Kondo | A61B 5/02438 600/344 |
| 2004/0032728 A1 * | 2/2004 | Galli | F21S 48/115 362/84 |
| 2005/0075549 A1 * | 4/2005 | Kondoh | A61B 5/0059 600/323 |
| 2006/0197753 A1 | 9/2006 | Hotelling | |
| 2008/0097221 A1 * | 4/2008 | Florian | A61B 5/02433 600/476 |
| 2008/0228089 A1 * | 9/2008 | Cho | A61B 5/021 600/485 |
| 2009/0018452 A1 * | 1/2009 | Sugiura | A61B 5/02433 600/476 |
| 2013/0123591 A1 * | 5/2013 | Naganuma | A61B 5/0095 600/316 |
| 2013/0207851 A1 * | 8/2013 | Dabov | H01Q 1/243 343/702 |
| 2014/0121471 A1 * | 5/2014 | Walker | A61B 5/1128 600/301 |
| 2014/0127996 A1 * | 5/2014 | Park | H04W 4/027 455/41.1 |
| 2014/0142403 A1 * | 5/2014 | Brumback | A61B 5/02433 600/324 |
| 2014/0155705 A1 | 6/2014 | Papadopoulos et al. | |
| 2014/0275852 A1 * | 9/2014 | Hong | A61B 5/02427 600/301 |
| 2014/0361147 A1 * | 12/2014 | Fei | G01J 1/0407 250/206 |
| 2014/0378844 A1 * | 12/2014 | Fei | A61B 5/02427 600/476 |
| 2016/0058313 A1 * | 3/2016 | Sato | A61B 5/02438 600/508 |
| 2016/0327921 A1 * | 11/2016 | Ribbich | F24F 11/0086 |

FOREIGN PATENT DOCUMENTS

| | | | |
|---|---|---|---|
| WO | WO-2014/043410 A1 | 3/2014 | |
| WO | WO 2014043410 A1 * | 3/2014 | F21V 7/0033 |
| WO | WO-2015/094378 A1 | 6/2015 | |
| WO | WO-2016/032682 A1 | 3/2016 | |

OTHER PUBLICATIONS

Spigulis, J. et al. (Apr. 25, 2008). "Wearable wireless photoplethysmography Sensors," Institute of Atomic Physics and Spectroscopy, University of Latvia, Proc. of SPIE, vol. 6991, pp. 699120-699120-7, XP055223673.

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI ' 92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

* cited by examiner

REFLECTIVE SURFACES FOR PPG SIGNAL DETECTION

FIELD

This relates generally to a device that measures a photoplethysmographic (PPG) signal, and, more particularly, to reflective surfaces for PPG signal detection.

BACKGROUND

A photoplethysmographic (PPG) signal can be measured by PPG systems to derive corresponding physiological signals (e.g., pulse rate). In a basic form, PPG systems can employ a light source or light emitter that injects light into the user's tissue, and a light detector to receive light that reflects and/or scatters and exits the tissue. The received light includes light with amplitude that is modulated as a result of pulsatile blood flow (i.e., "signal") and parasitic, non-signal light with amplitude that can be modulated (i.e., "noise" or "artifacts") and/or unmodulated (i.e., DC). However, in some examples, the reflected and/or scattered light received by the light detector may be have a low signal strength, making it difficult to accurately determine the user's pulse rate.

One way to increase the signal intensity or signal strength can be to decrease the distance between the light sensor and light emitter. The minimum distance between the light sensor and light emitter can, however, be limited by mechanical or functional requirements of other components on the PPG system, such as the windows used to cover and protect the light source and light detector. An alternative way to increase the signal strength may be needed.

SUMMARY

This relates to reflective surfaces around the apertures of PPG optical components in PPG systems. In a PPG system or device, the addition of reflective surfaces around, under, or near the apertures of the optical components can enhance the amount of light received by the light detector. As a result, the measured PPG signal strength can be higher and more accurate compared to the same PPG device without reflective surfaces. The reflective surfaces can reflect and/or recycle light that is incident upon the reflective surfaces back into the skin for eventual capture of the light by the light detectors.

DETAILED DESCRIPTION

In the following description of examples, reference is made to the accompanying drawings in which it is shown by way of illustration specific examples that can be practiced. It is to be understood that other examples can be used and structural changes can be made without departing from the scope of the various examples.

In the following description, numerous specific details are set forth in order to provide a thorough understanding of one or more aspects and/or features described or referenced herein. It will be apparent, however, to one skilled in the art, that one or more aspects and/or features described or referenced herein may be practiced without some or all of these specific details.

A photoplethysmographic (PPG) signal can be measured by PPG systems to derive corresponding physiological signals (e.g., pulse rate). Such PPG systems can be designed to be sensitive to changes in blood in a user's tissue that can result from fluctuations in the amount or volume of blood or blood oxygen in the vasculature of the user. In a basic form, PPG systems can employ a light source or light emitter that injects light into the user's tissue, and a light detector to receive light that reflects and/or scatters and exits the tissue. The PPG signal is the amplitude of reflected and/or scattered light that is modulated with volumetric change in blood volume in the tissue. However, in some examples, some of the reflected and/or scattered light can be lost, leading to a PPG signal measured by the light detector having a low signal strength. As a result, it may be difficult to accurately determine the user's physiological state.

This disclosure relates to reflective surfaces around, under, on or near one or more apertures of the PPG optical components. In a PPG device, the addition of reflective surfaces around, under, on or near the apertures of the optical components can enhance signal strength compared to the same PPG device without reflective surfaces. The reflective surfaces can reflect or recycle light that is incident upon the reflective surfaces back into the skin for eventual capture of the light by the light detectors. This incident light may not have been as effectively reflected (if at all) without the reflective surfaces, and could therefore be lost (i.e., not contribute to the signal measured by the light detector).

Representative applications of methods and apparatus according to the present disclosure are described in this section. These examples are being provided solely to add context and aid in the understanding of the described examples. It will thus be apparent to one skilled in the art that the described examples may be practiced without some or all of the specific details. Other applications are possible, such that the following examples should not be taken as limiting.

Figure 1:
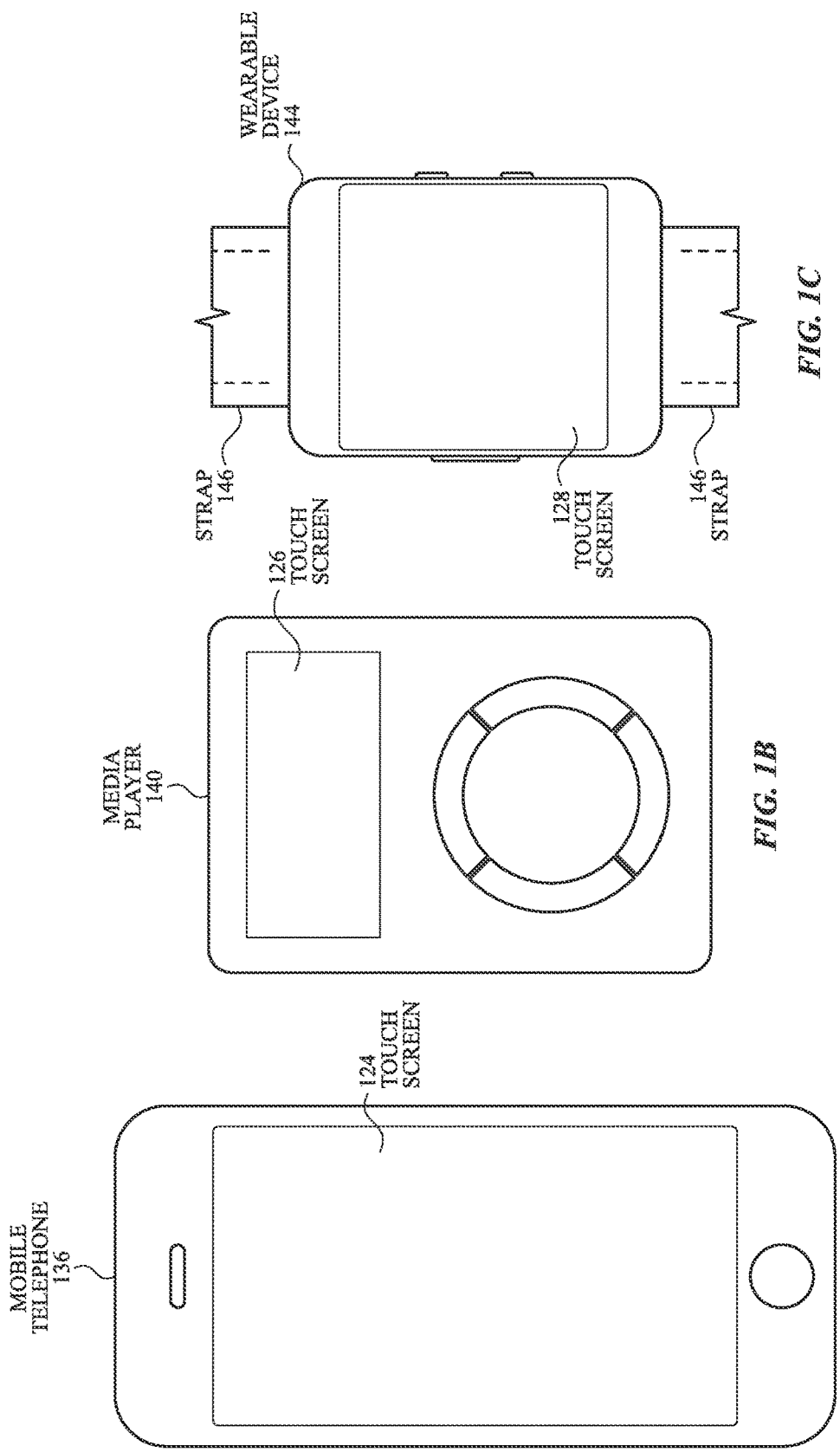
FIGS. 1A-1C illustrate systems in which examples of the disclosure can be implemented.

FIGS. 1A-1C illustrate systems in which examples of the disclosure can be implemented. FIG. 1A illustrates an exemplary mobile telephone 136 that can include a touch screen 124. FIG. 1B illustrates an exemplary media player 140 that can include a touch screen 126. FIG. 1C illustrates an exemplary wearable device 144 that can include a touch screen 128 and can be attached to a user using a strap 146. The systems of FIGS. 1A-1C can utilize the reflective surfaces as will be disclosed.

Figure 2:
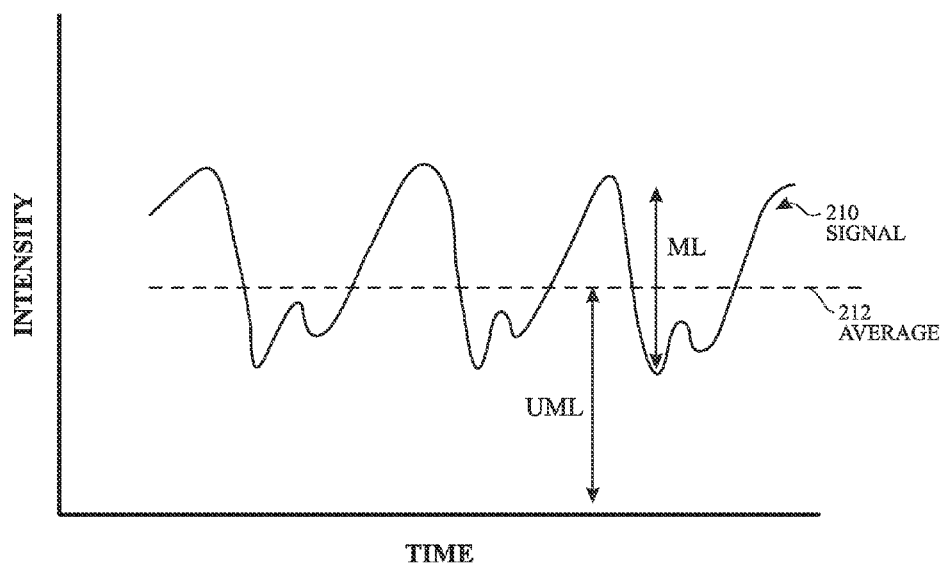
FIG. 2 illustrates an exemplary PPG signal according to examples of the disclosure.

FIG. 2 illustrates an exemplary PPG signal absent of artifacts. Signal 210 can be light measured by one or more light detectors and processed such that artifacts are optionally removed or extracted from the signal. Signal 210 can include light information with an amplitude that is modulated as a result of pulsatile blood flow (i.e., "signal") and parasitic, unmodulated, non-signal light (i.e., DC). From the measured PPG signal 210, a perfusion index can be determined. The perfusion index can be the ratio of received modulated light (ML) to unmodulated light (UML) (i.e., ratio of blood flow modulated signal to static, parasitic DC signal) and can give extra information regarding the user's physiological state. The modulated light (ML) can be the peak-to-valley value of signal 210, and unmodulated light (UML) can be the zero-to-average (using average 212) value of signal 210. As shown in FIG. 2, the perfusion index can be equal to the ratio of ML to UML.

Figure 3A:
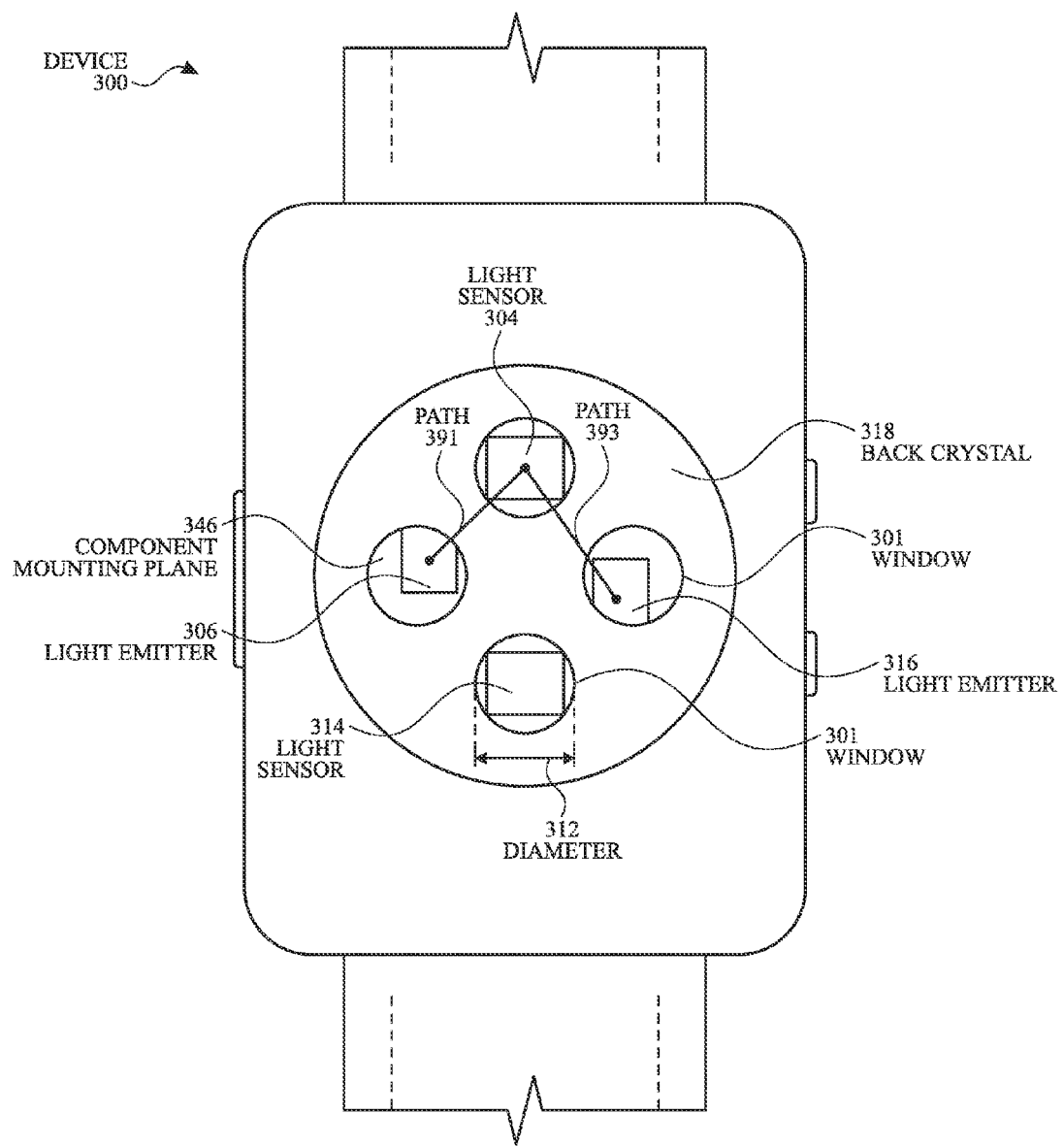
FIG. 3A illustrates a top view of an exemplary electronic device configured to measure a PPG signal according to examples of the disclosure.
Figure 3B:
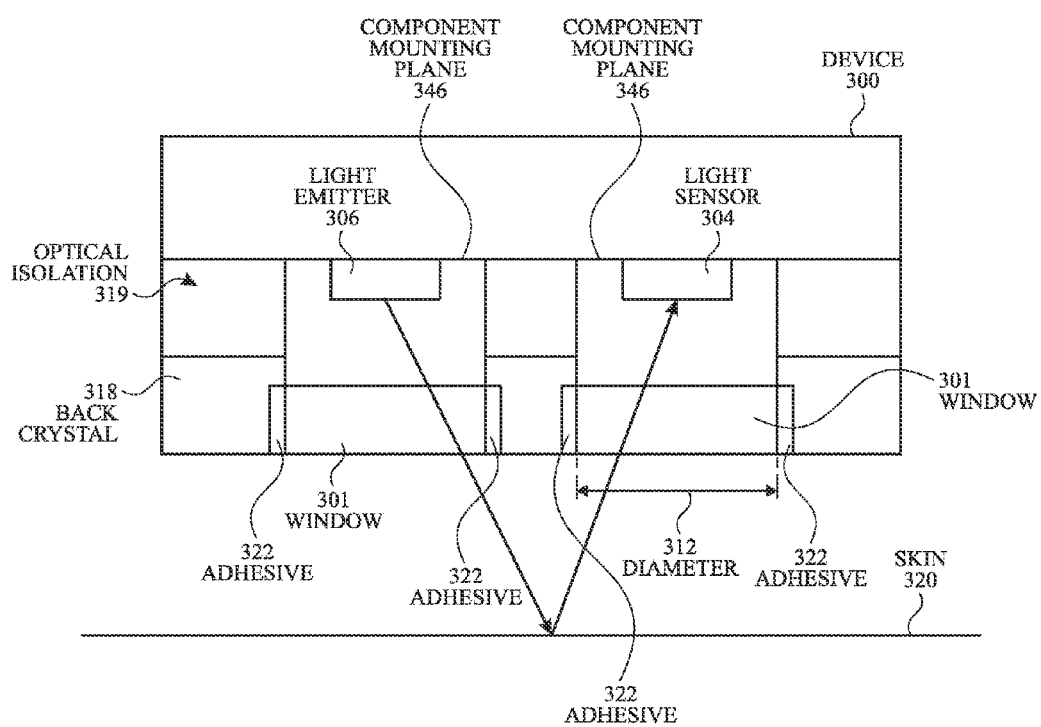
FIG. 3B illustrates a cross-sectional view of an exemplary electronic device configured to measure a PPG signal according to examples of the disclosure.

FIG. 3A illustrates a top view, and FIG. 3B illustrates a cross-sectional view of an exemplary electronic device configured to measure a PPG signal. Device 300 can include light emitters 306 and 316 and light sensors 304 and 314 located on a surface of device 300. Light emitters 306 and 316 and light sensors 304 and 314 can be facing towards a skin 320 of a user. Between light emitter 306 (or any one or more of light emitter 316 and light sensors 304 and 314) and skin 320 can be windows 301 surrounded by back crystal 318. Windows 301 can have a diameter 312 and can be mounted to device 300 using an adhesive 322 on the sides of windows 301. Device 300 can optionally include optical isolation 319. Light emitters 306 and 316 can be any type of light source, including but not limited to, light emitting diodes (LEDs), incandescent lights, fluorescent lights, organic light emitting diodes (OLEDs), and electroluminescent diodes (ELDs). Light sensors 304 and 314 can be any type of optical sensing device such as a photodiode. In some examples, light emitters 306 and 316 and/or light sensors 304 and 314 can be mounted or touching a component mounting plane 346. In some examples, either light sensors 304 and 314 or light emitters 306 and 314 or both can be symmetrically placed with respect to the center of the back crystal 318. In some examples, either light sensors 304 and 314 or light emitters 306 and 316 or both can be asymmetrically placed with respect to the center of the back crystal 318.

Figure 4A:
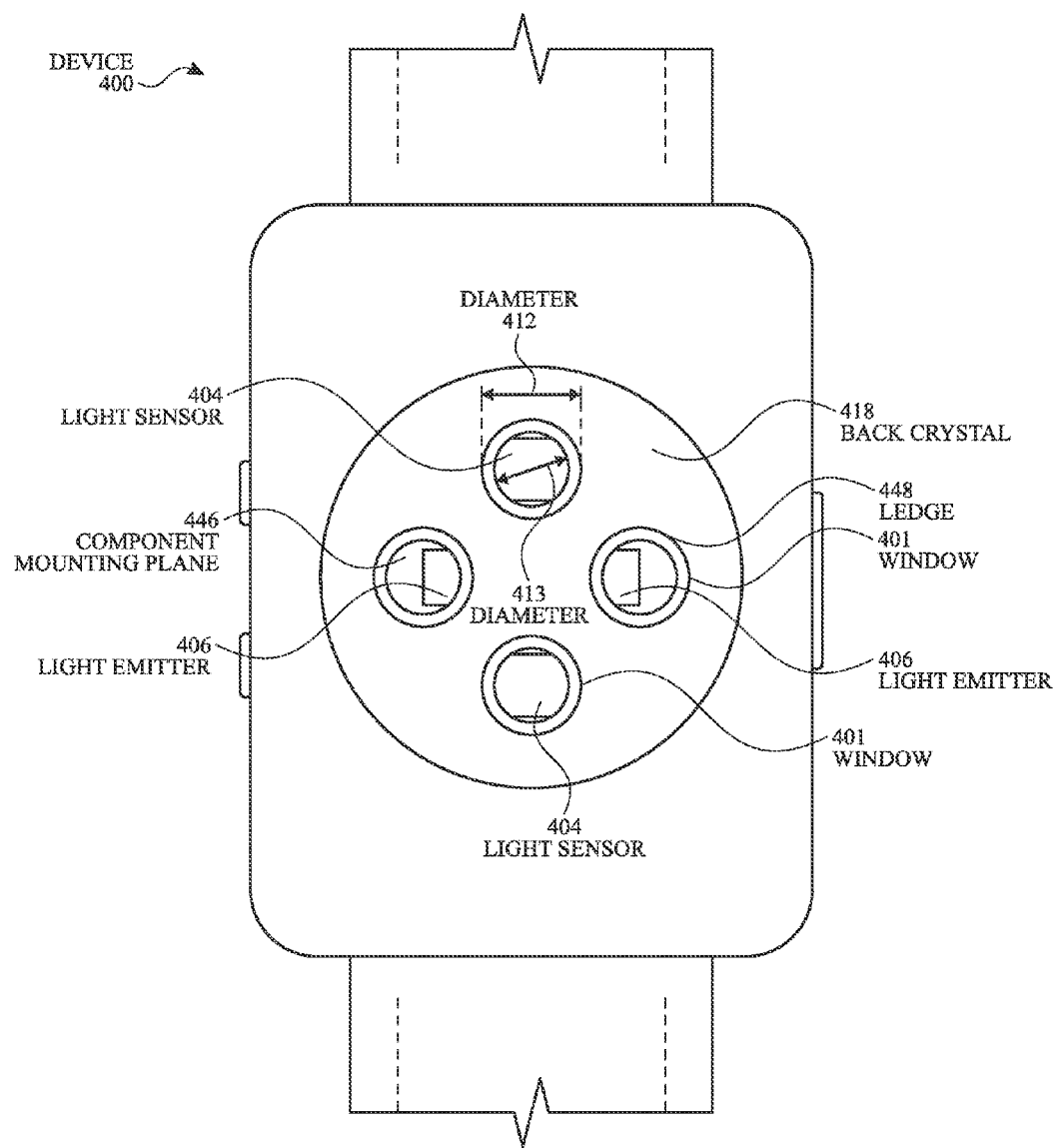
FIG. 4A illustrates a top view of an exemplary electronic device with ledges configured to measure a PPG signal according to examples of the disclosure.
Figure 4B:
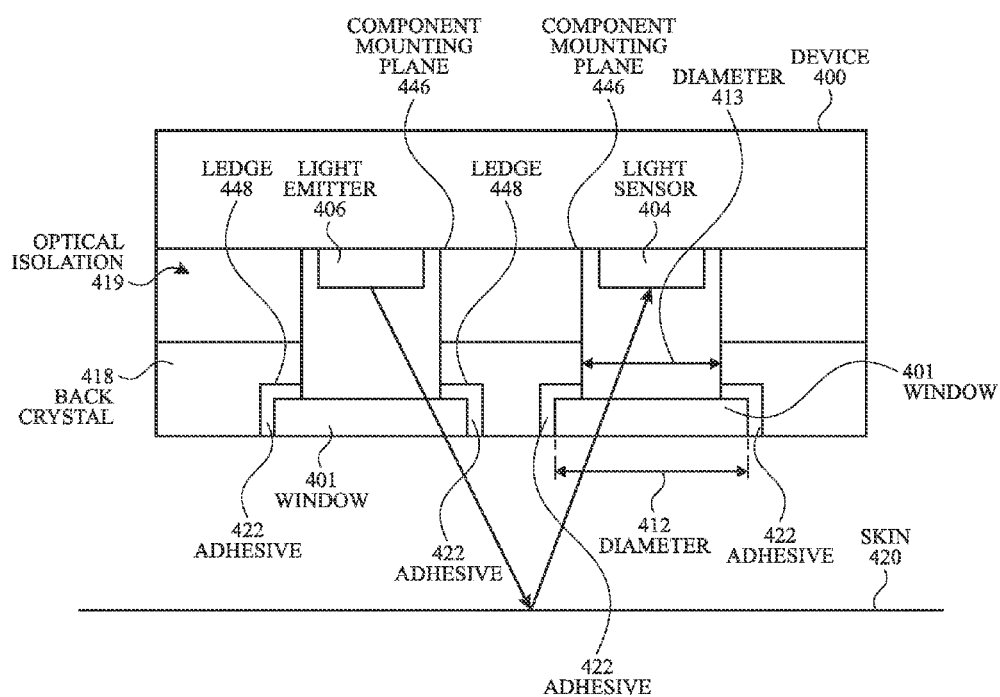
FIG. 4B illustrates a cross-sectional view of an exemplary electronic device with ledges configured to measure a PPG signal according to examples of the disclosure.

In some examples, adhesive 322 applied to the sides of the windows 301 can be insufficient for effectively attaching windows 301 to device 300. For such a case, back crystal 318 can be designed to improve mechanical stability. FIG. 4A illustrates a top view, and FIG. 4B illustrates a cross-sectional view of an exemplary electronic device configured to measure a PPG signal according to examples of the disclosure. Device 400 can include light emitters 406 and light sensors 404 located on a surface of device 400. Light emitters 406 and light sensors 404 can be facing towards a skin 420 of a user and can be mounted to or touching a component mounting plane 446. In some examples, light emitters 406 can be y-centered (i.e., symmetrically placed along the horizontal axis). Between light emitters 406 (or light sensors 404) and skin 420 can be windows 401 surrounded by back crystal 418. Back crystal 418 can include ledges 448 for improving the mechanical stability of device 400 by providing a larger surface area for windows 401 to rest on and/or adhere to. Windows 401 can have a diameter 412 and can be mounted to device 400 using an adhesive 422 to attach the sides of windows 401 and at least a portion of one side of windows 401 to ledges 448. While back crystal 418 can improve the adhesion of windows 401 to back crystal 418, the ledges 448 may lead to a smaller aperture or diameter 413 than for devices without a ledge (such as illustrated in FIGS. 3A-3B). Device 400 can optionally include optical isolation 419.

Figure 4C:
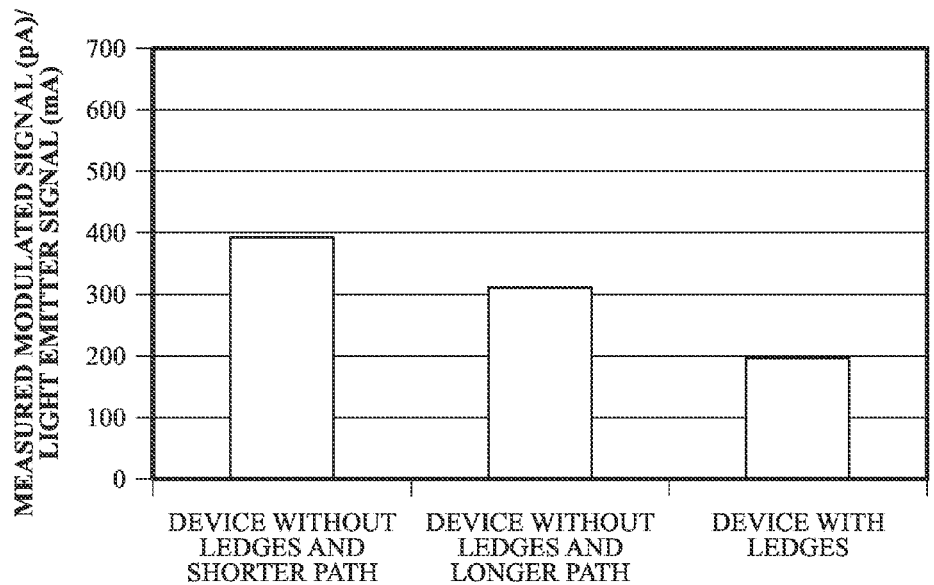
FIGS. 4C-4F illustrate bar charts of measured modulated light, unmodulated light, perfusion index and signal-to-noise ratio of an exemplary device without ledges and an exemplary device with ledges according to examples of the disclosure.

The smaller diameter 413 can lead to a lower amount of light reaching skin 420 from light emitters 406 and/or a lower amount of light reflecting or scattering back and being sensed by light sensors 404. As a result, the light intensity and measured signal strength may be reduced. FIG. 4C illustrates a bar chart of measured modulated light of an exemplary device without ledges and an exemplary device with ledges according to examples of the disclosure. A device with ledges (such as device 400 shown in FIGS. 4A-4B) can have a lower modulated light signal than a device without ledges (such as device 300 shown in FIGS. 3A-3B). As discussed above, the lower modulated light signal can be due to a change in aperture size. For example, diameter 312 or 412 can be 6.1 mm, and diameter 413 can be 3.9 mm. In the present example, ledges 448 in device 400 can lead to an optical aperture that can be reduced by 2.2 mm in diameter or 69.12 mm² in area. The device without ledges (device 300) can have a modulated light signal value of 392 pA/mA from the shorter path (path 391) and a modulated light signal value of 309 pA/mA from the longer path (path 393). The device with ledges (device 400) can have a modulated light signal value of 197 pA/mA, which is at least 50% lower than the modulated light signal values of the device without ledges (device 300).

Figure 4D:
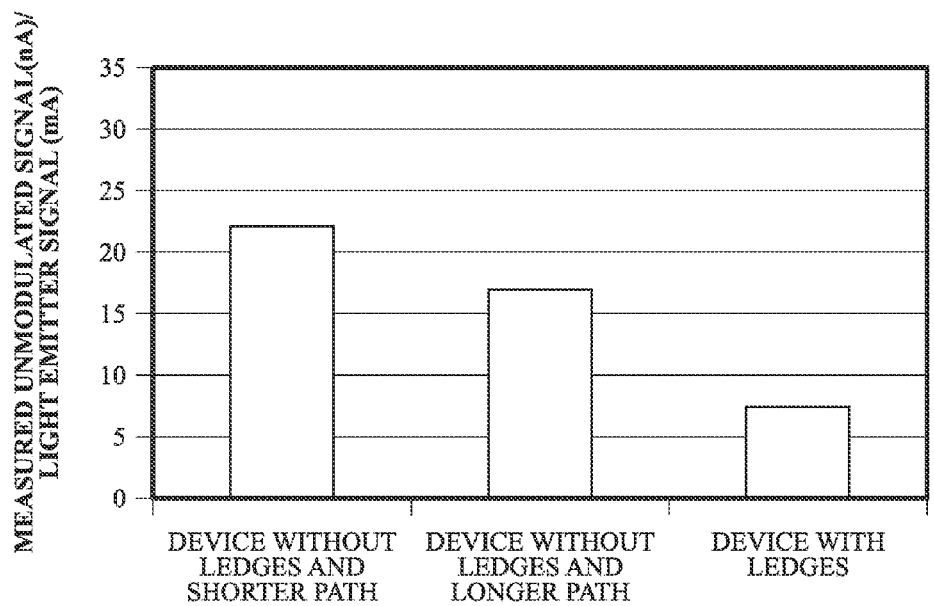

In addition to a lower modulated light signal, ledges 448 in device 400 can result in a lower unmodulated light signal as shown in FIG. 4D. For example, the device without ledges (device 300) can have an unmodulated light signal value of 22.2 nA/mA from path 391 and an unmodulated light signal value of 17.0 nA/mA from path 393. The device with ledges (device 400) can have an unmodulated light signal value of 7.5 nA/mA, which is at least 55% lower than the unmodulated light signal values of the device without ledges (device 300).

Figure 4E:
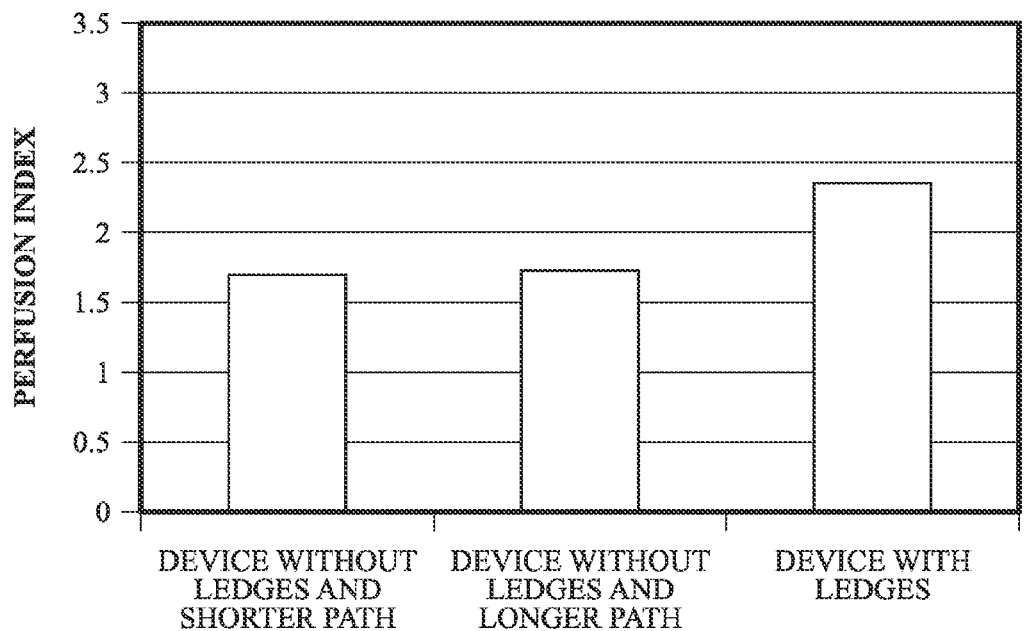

As discussed above, the perfusion index is equal to the ratio of modulated light to unmodulated light. FIG. 4E illustrates a bar chart of the perfusion index of an exemplary device without ledges and an exemplary device with ledges according to examples of the disclosure. Although the device without ledges (device 300) can have a higher modulated light signal and a higher unmodulated light signal than a device with ledges (device 400), the perfusion index can be lower. For example, the device without ledges (device 300) can have a perfusion index from the shorter path (path 391) of 1.7% and a perfusion index from the longer path (path 393) of 1.73%, whereas the device with ledges (device 400) can have a perfusion index of 2.36%.

Figure 4F:
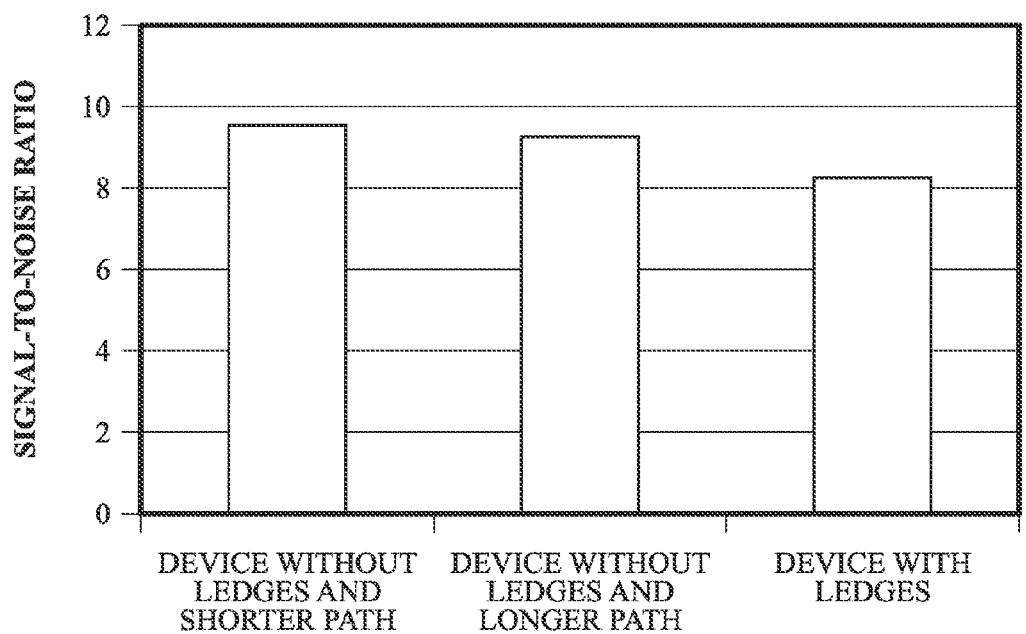

Additionally, the device with ledges (device 400) can have a lower signal-to-noise ratio than the device without ledges (device 300), as illustrated in FIG. 4F. For example, the shorter path (path 391) of the device without ledges (device 300) can have a signal-to-noise ratio of 9.6 bits, and the longer path (path 393) of the device without ledges (device) 300 can have a signal-to-noise ratio of 9.3 bits. The device with ledges (device 400) can have a lower signal-to-noise ratio value of 8.3 bits.

Figure 5A:
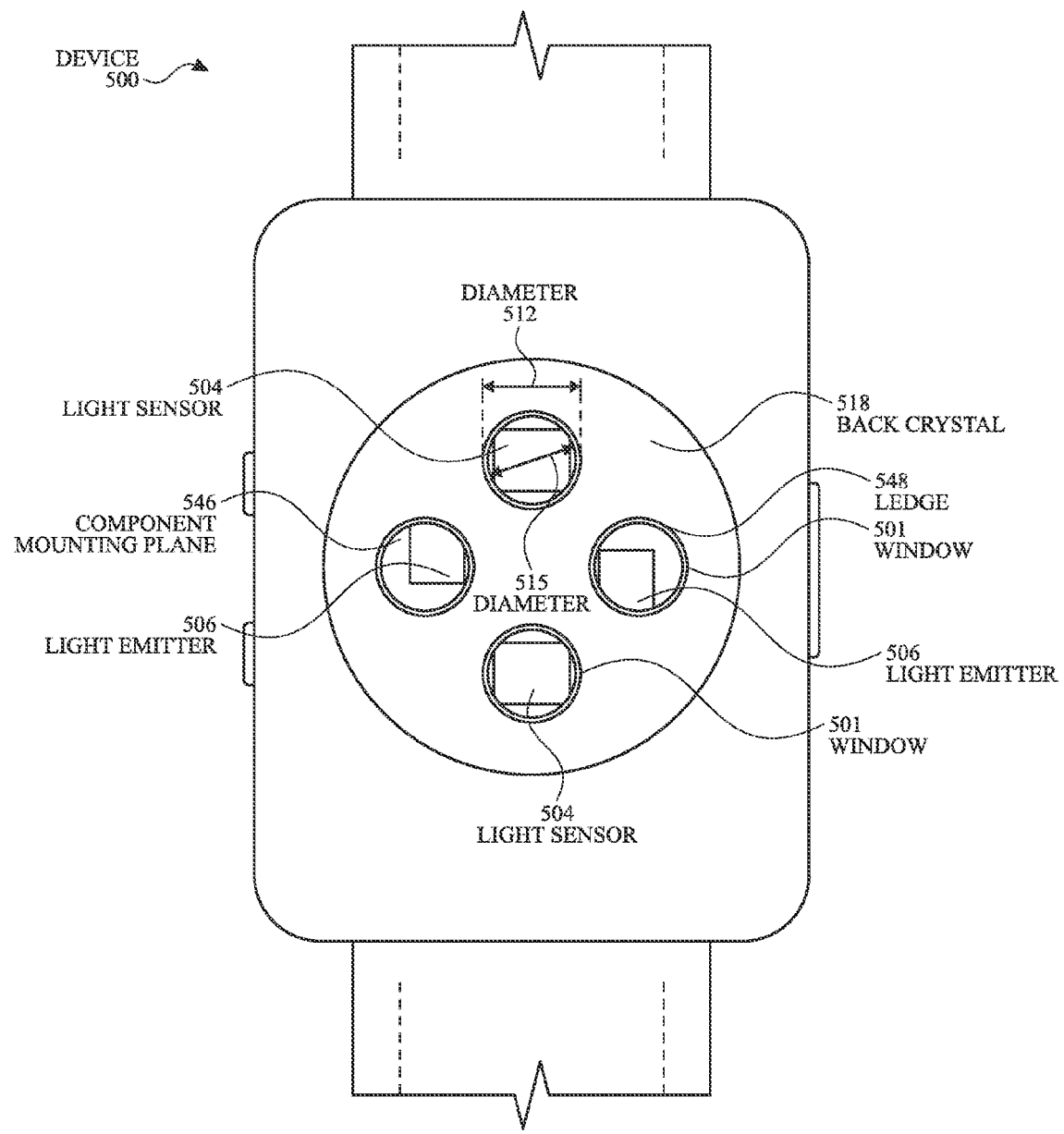
FIG. 5A illustrates a top view of an exemplary electronic device with increased aperture sizes configured to measure a PPG signal according to examples of the disclosure.
Figure 5B:
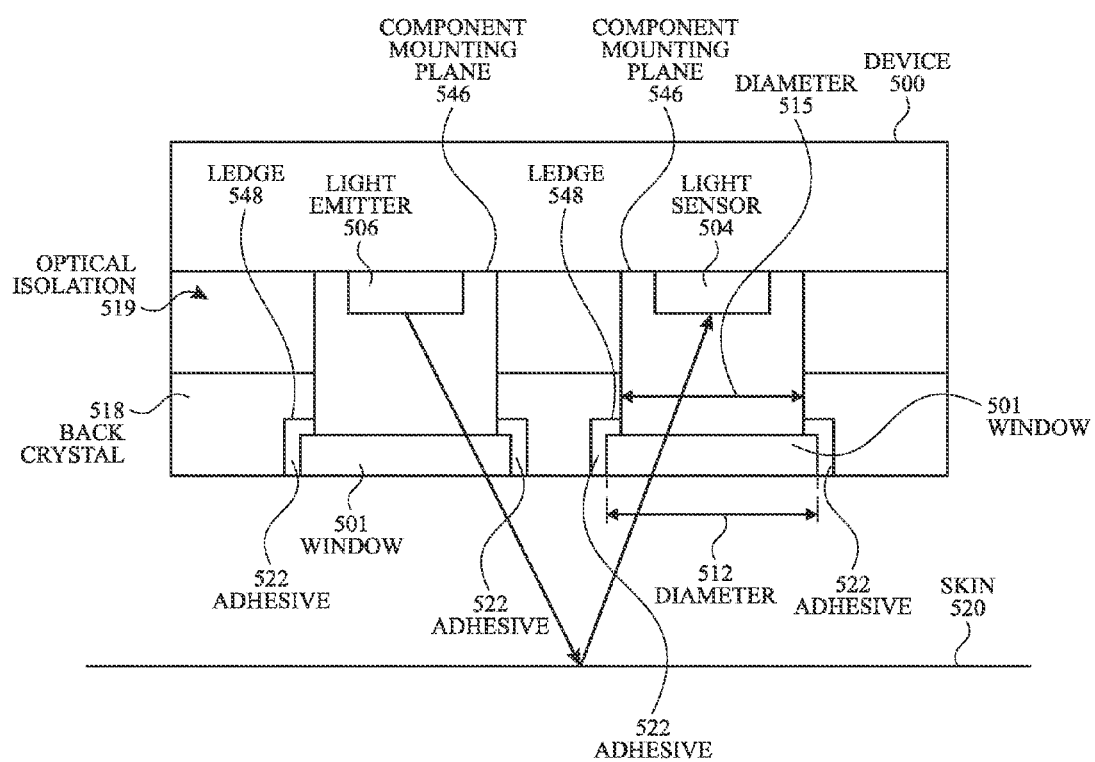
FIG. 5B illustrates a cross-sectional view of an exemplary electronic device with increased aperture sizes configured to measure a PPG signal according to examples of the disclosure.

As illustrated in FIGS. 4C-4F, the device with ledges can lead to a reduced signal intensity. However, removing the ledges or manufacturing a device without ledges can result in a device with poor mechanical stability to secure or attach the windows. A different method to increasing the signal intensity may be needed. FIG. 5A illustrates a top view, and FIG. 5B illustrates a cross-sectional view of an exemplary electronic device configured to measure a PPG signal according to examples of the disclosure. Device 500 can include light emitters 506 and light sensors 504 attached to or touching component mounting plane 546. Device 500 can optionally include optical isolation 519. Windows 501 with a diameter 512 can be included for covering and/or protecting light emitters 506 and light sensors 504. Back crystal 518 can be disposed around windows 501. Windows 501 can be touching or attached (using adhesive 522) to ledges 548. Light can be emitted from light emitters 506 towards a skin 520 of a user. Light can reflect and/or scatter off skin 520, vasculature, and blood of the user and reflect back towards light sensor 504. To increase the signal intensity, a diameter 515 of the apertures can be made larger than diameter 413 of FIGS. 4A-4B.

Figure 5C:
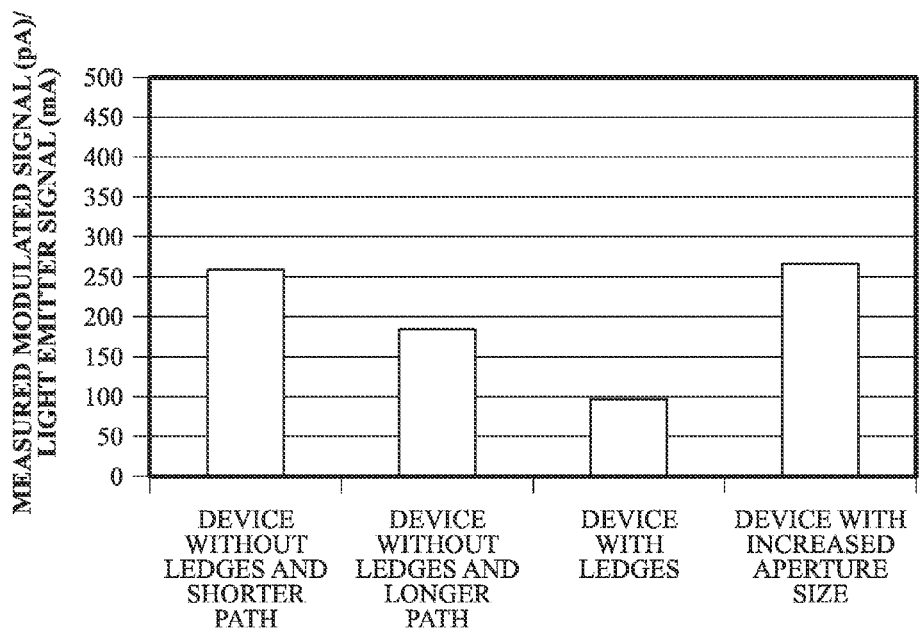
FIGS. 5C-5F illustrate bar charts of measured modulated light values, unmodulated light values, perfusion index and signal-to-noise ratio values for an exemplary device without ledges, an exemplary device with ledges, and an exemplary device with increased aperture sizes according to examples of the disclosure.
Figure 5D:
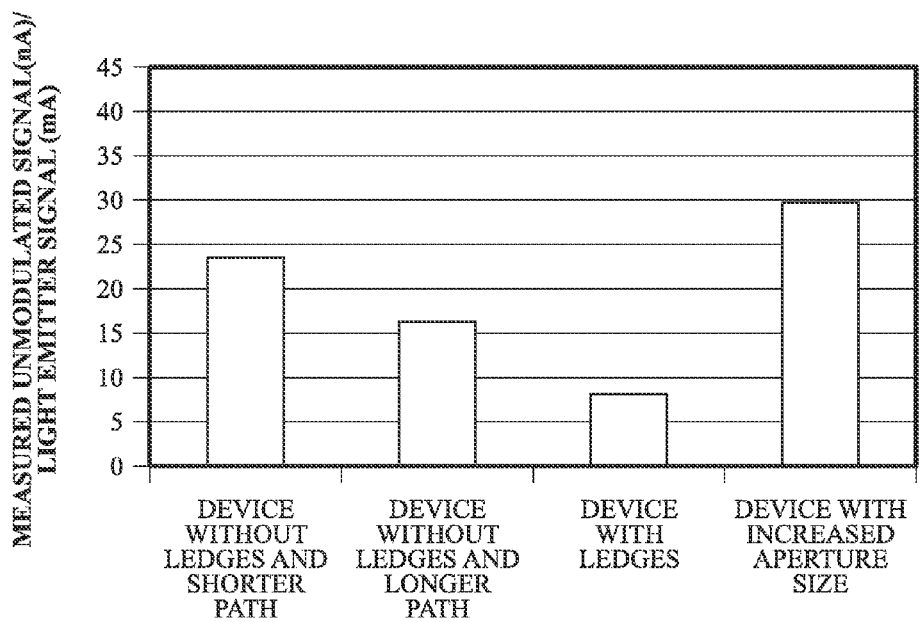

FIGS. 5C-5F illustrate bar charts of measured modulated light values, unmodulated light values, perfusion index, and signal-to-noise ratio values for an exemplary device without ledges (device 300 of FIGS. 3A-3B), an exemplary device with ledges (device 400 of FIGS. 4A-4B), and an exemplary device with increased aperture size (device 500 of FIGS. 5A-5B) according to examples of the disclosure. For example, a diameter 515 of the device with increase aperture size (device 500) can be 4.9 mm, whereas a diameter 413 of the device with ledges (device 400) can be 3.9 mm. In some examples, the device with increased aperture size (device 500) can include ledges. The increased aperture size (device 500) can lead to an increase in measured modulated light values. As shown in FIG. 5C, the device without ledges (device 300) can have a modulated light signal value of 257 pA/mA from the shorter path (path 391) and a modulated light signal value of 181 pA/mA from longer path (path 393). The addition of ledges 448 (device 400) can lead to a lower modulated light signal value of 94 pA/mA. However, the reduced intensity can be compensated by increasing the aperture size (device 500). The device with increased aperture size (device 500) can have a modulated light signal value of 262 pA/mA, which is comparable to device 300 (the device without ledges). As shown in FIG. 5D, increasing the aperture size can also result in measured unmodulated light values for the device with increased aperture size (device 500) higher than measured unmodulated light values for the device without ledges (device 300). For example, the unmodulated light values for the device without ledges (device 300) can be 23.6 nA/mA for the shorter path (path 391) or 16.2 nA/mA for the longer path (path 393), 7.9 nA/mA for the device with ledges (device 400), and 29.7 nA/mA for the device with increase aperture size (device 500). Although increasing the aperture size can lead to a higher signal strength for measured modulated light, the measured unmodulated light (or noise) can increase as well.

Figure 5E:
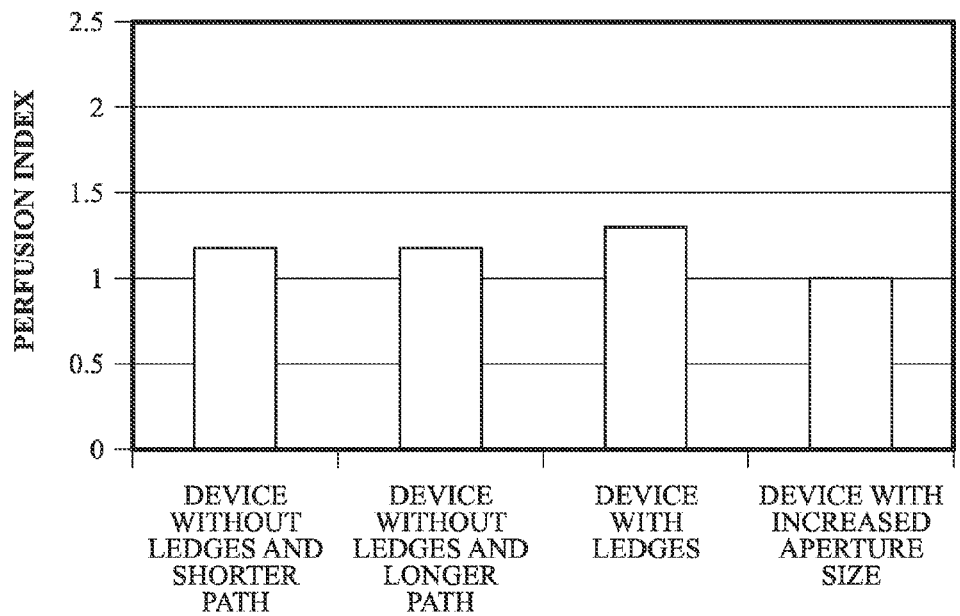
Figure 5F:
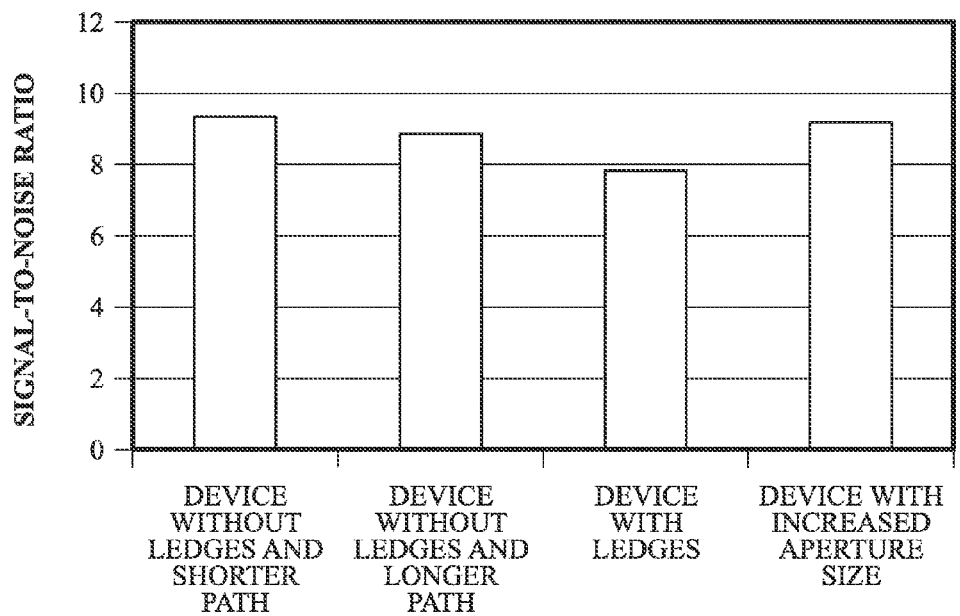

FIG. 5E illustrates an exemplary bar chart for perfusion index. The device without ledges (device 300) can have a perfusion index of 1.16-1.17%, the device with ledges (device 400) can have a perfusion index of 1.29%, and the device with increased aperture size (device 500) can have a perfusion index of 1.01%. Although the signal strength for modulated light increases, the perfusion index can be lower for the device with increase aperture size (device 500) due to the measured unmodulated light value also increasing. FIG. 5F illustrates comparable signal-to-noise ratio values for the device without ledges (device 300) and the device with ledges (device 500). The device without ledges (device 300) can have a signal-to-noise ratio value of between 8.9-9.4 bits. The device with ledges (device 400) can have a lower signal-to-noise ratio of 7.9 bits, while the device with increased aperture size (device 500) can have a signal-to-noise ratio of 9.2 bits.

Figure 6A:
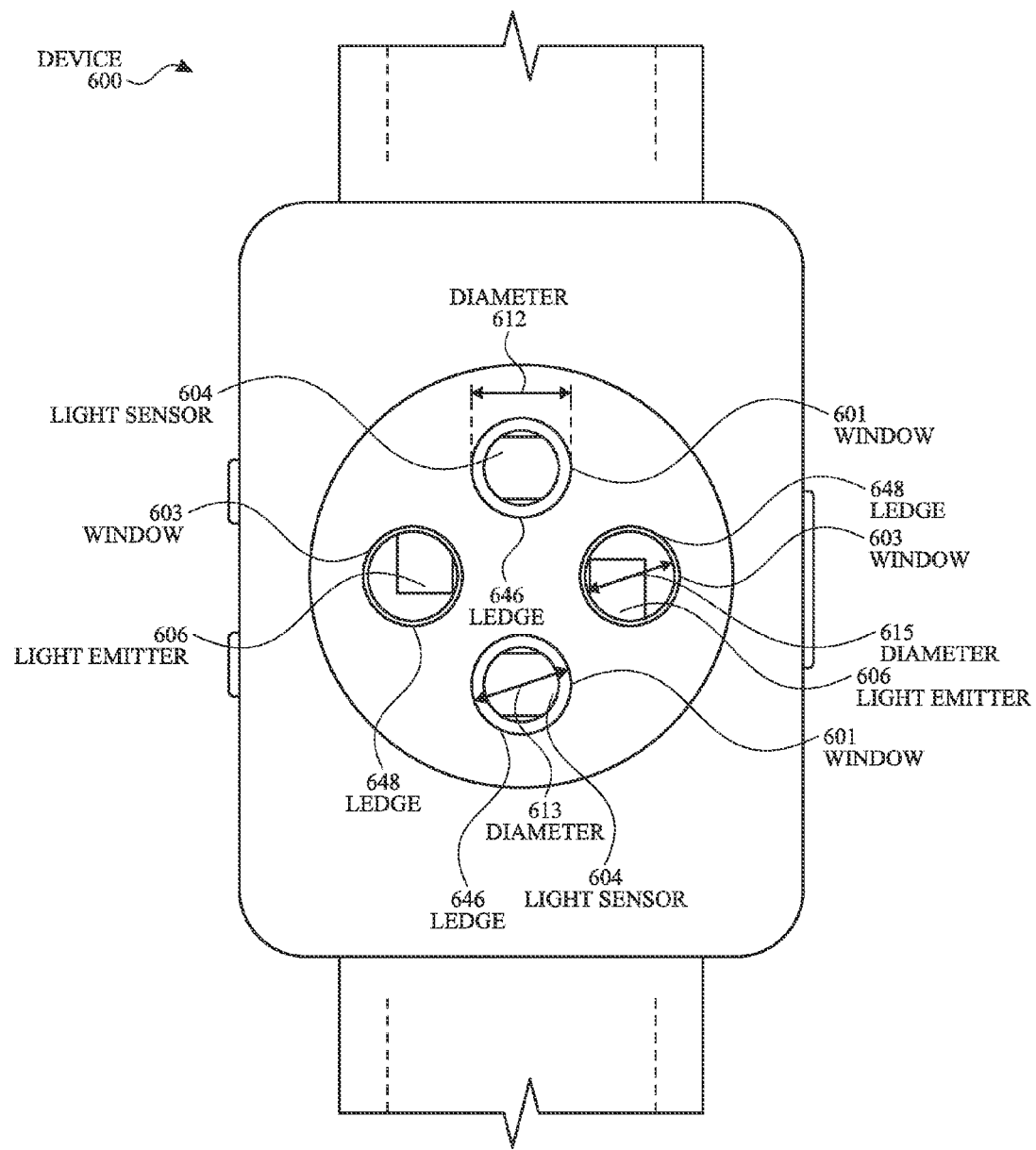
FIGS. 6A-6B illustrate top views of exemplary electronic devices with different aperture sizes configured to measure a PPG signal according to examples of the disclosure.
Figure 6B:
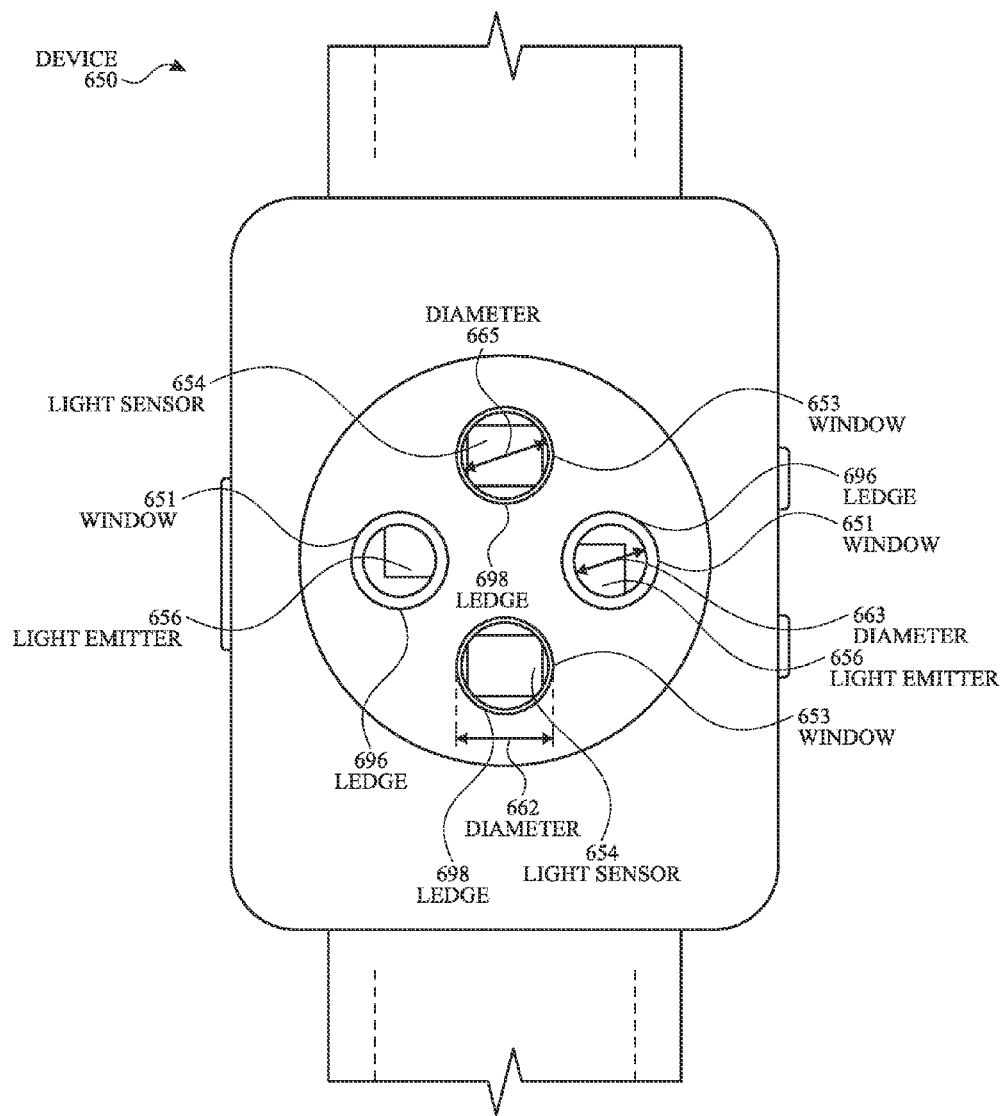

FIGS. 6A-6B illustrate top views of exemplary electronic devices with different aperture sizes configured to measure a PPG signal according to examples of the disclosure. Device 600 of FIG. 6A can include light sensors 604 and windows 601 covering and/or protecting light sensors 604. Windows 601 can be attached to or touching ledges 646. The apertures associated with light sensors 604 and windows 601 can have a diameter 613. Device 600 can also include light emitters 606 and windows 603 covering and/or protecting light emitters 606. Windows 603 can be attached to or touching ledges 648. The apertures associated with light emitters 606 and windows 603 can have a diameter 615. In some examples, diameter 613 can be smaller than diameter 615 due to a size difference between ledges 646 and 648. That is, light sensors 604 can receive light through smaller sized apertures than light emitters 606 emit light.

Device 650 of FIG. 6B can include light sensors 654 and windows 653 covering and/or protecting light sensors 654. Windows 653 can be attached to or touching ledges 698. The apertures associated with light sensors 654 and windows 653 can have a diameter 665. Device 650 can also include light emitters 656 and windows 651 covering and/or protecting light emitters 656. Windows 651 can be attached to or touching ledges 696. The apertures associated with light emitters 656 and windows 651 can have a diameter 663. In some examples, diameter 663 can be smaller than diameter 665 due to a size difference between ledges 696 and 698. That is, light sensors 654 can receive light through larger sized apertures than light emitters 656 can emit light.

Figure 6C:
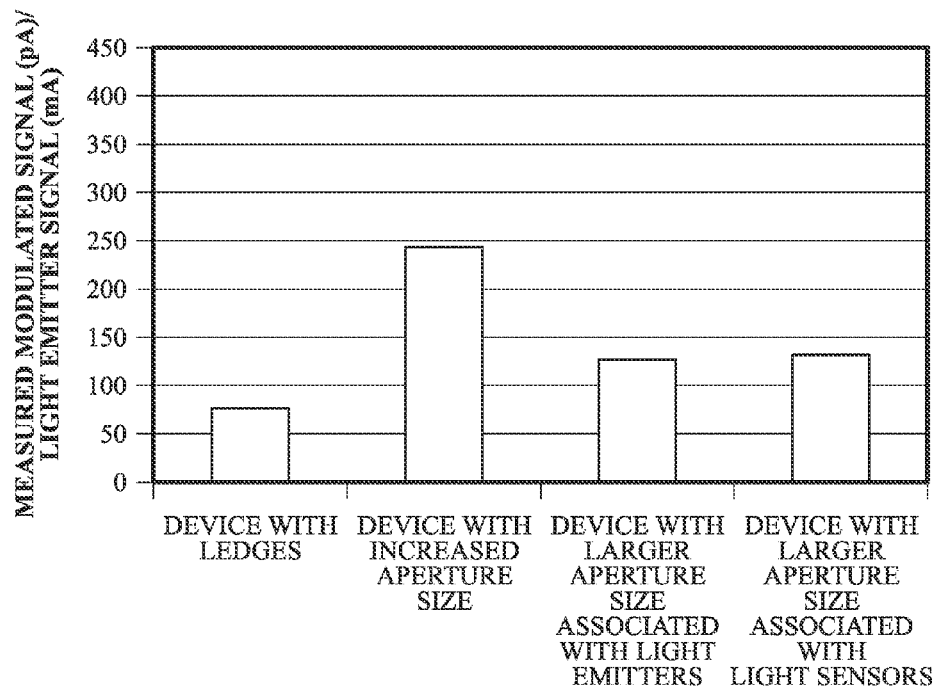
FIGS. 6C-6F illustrate bar charts of measured modulated light values, unmodulated light values, perfusion index and signal-to-noise ratio values for exemplary devices with different aperture sizes according to examples of the disclosure.
Figure 6D:
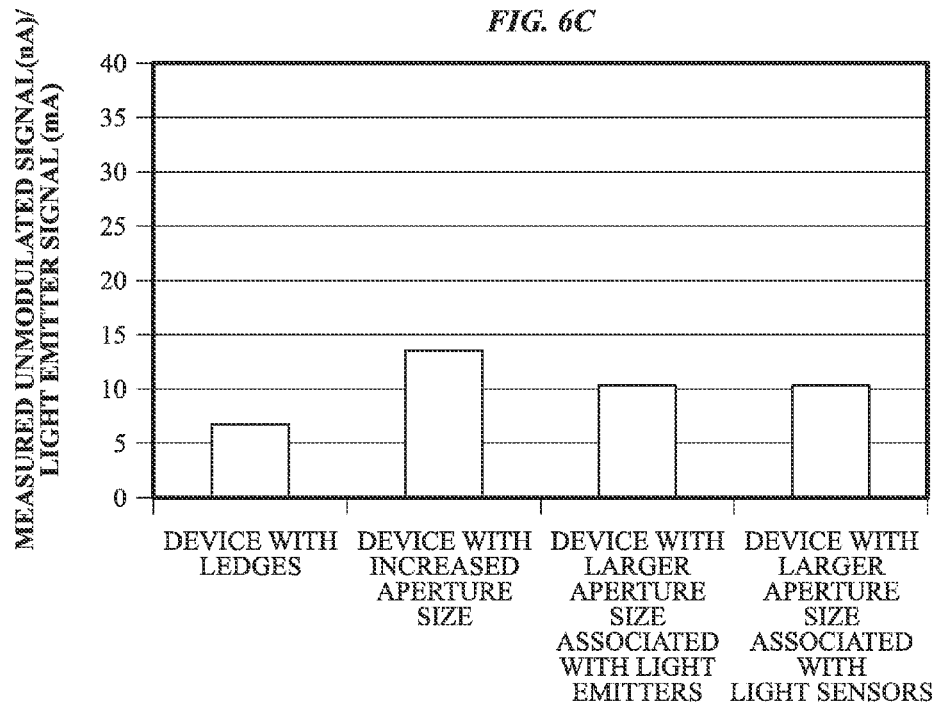
Figure 6E:
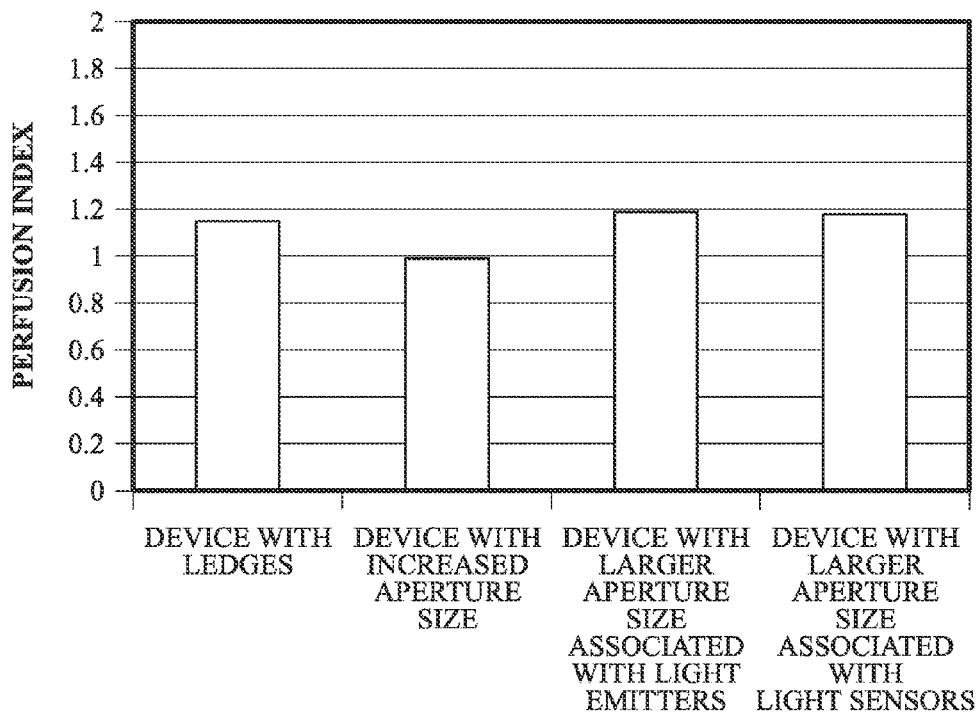
Figure 6F:
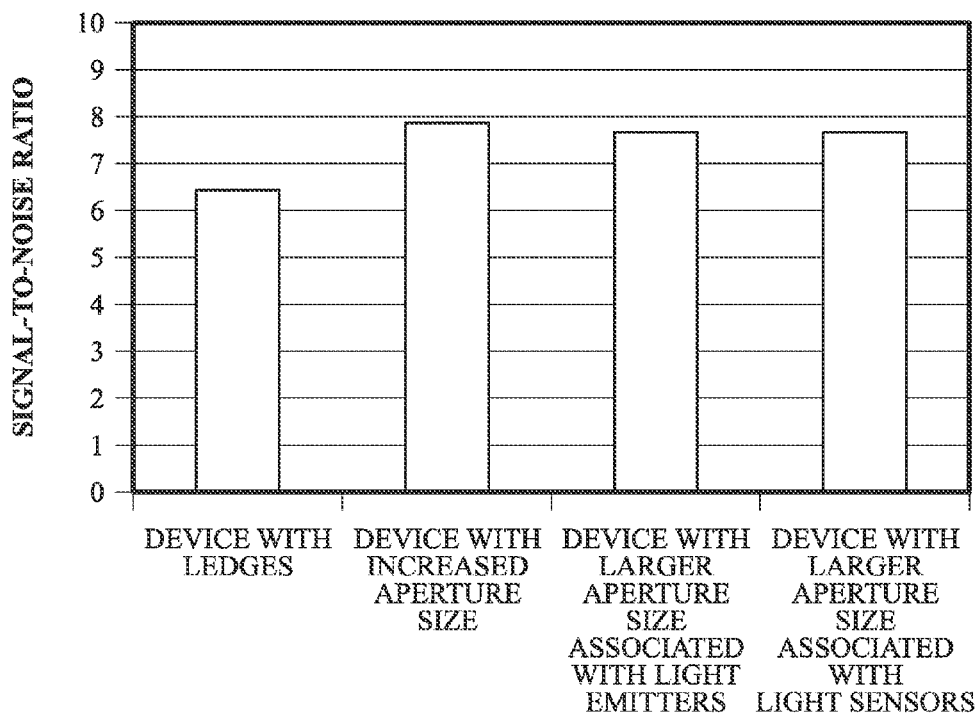

FIGS. 6C-6F illustrate bar charts of measured modulated light values, unmodulated light values, perfusion index and signal-to-noise ratio values for exemplary devices with different aperture sizes according to examples of the disclosure. For example, diameters 613 and 663 can be 3.9 mm, diameters 615 and 665 can be 4.9 mm, and diameters 612 and 662 of windows 612 can be 6.12 mm. As shown in FIG. 6C, the modulated light value is comparable for device 600 and 650. That is, selectively choosing which one of the light emitters 606 and 656 or light sensors 604 and 654 is associated with the larger sized aperture may not have a significant effect on the modulated light value. Similarly, as shown in FIG. 6D, the unmodulated light value is comparable for the device with larger aperture size associated with the light emitters (device 600) and for the device with larger aperture size associated with the light sensors (device 650). FIG. 6E shows comparable perfusion indices for the device with larger aperture size associated with the light emitters (device 600) and the device with larger aperture size associated with the light sensors (device 650), and FIG. 6F shows comparable signal-to-noise ratio values. The highest modulated light value and unmodulated light value can be achieved with device 500 (i.e., the device with largest aperture sizes for both light emitters and light sensors). However, device 500 can also have the lowest perfusion index and highest signal-to-noise ratio.

Figure 7A:
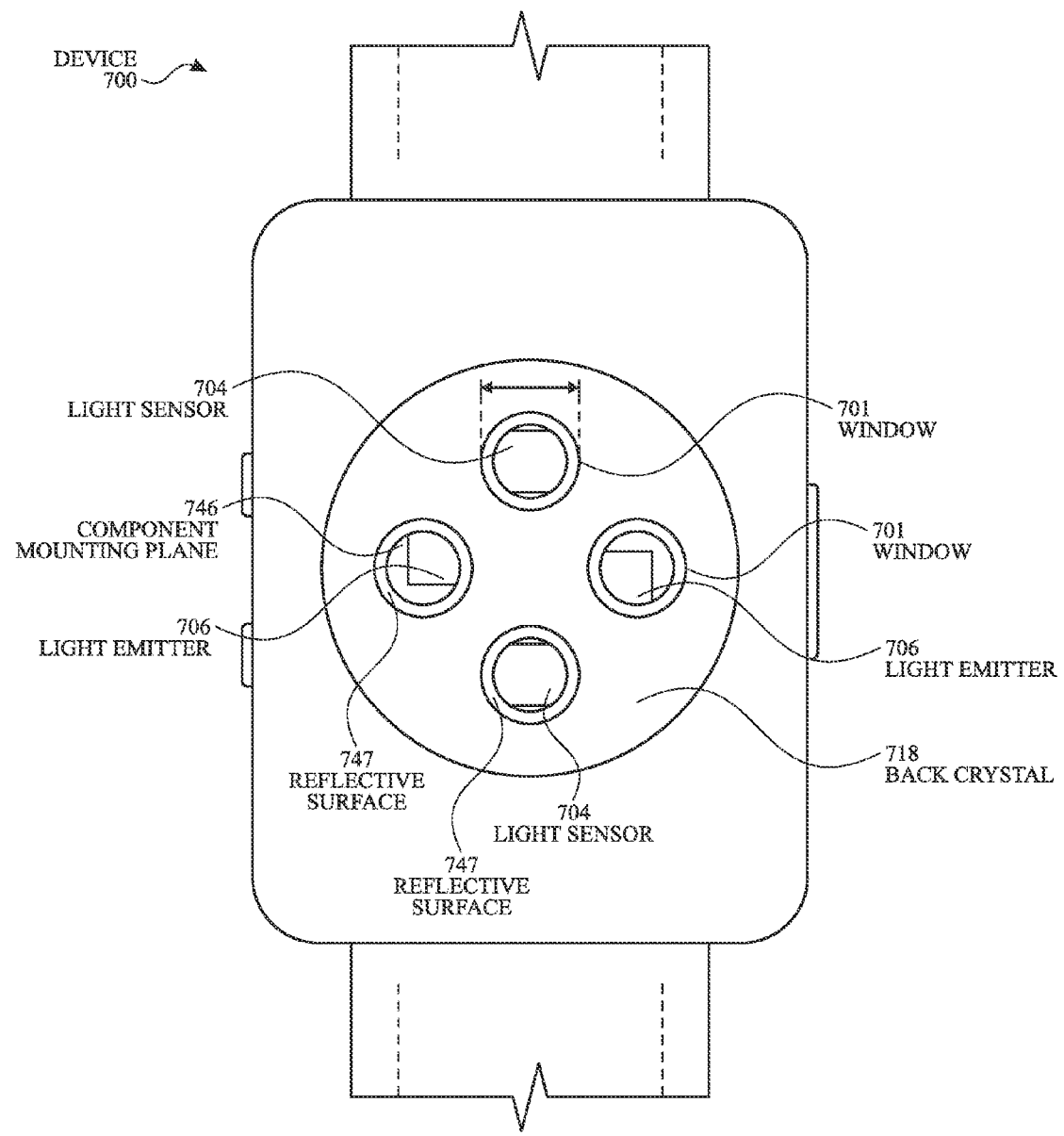
FIG. 7A illustrates a top view of an exemplary electronic device with reflective surfaces configured to measure a PPG signal according to examples of the disclosure.
Figure 7B:
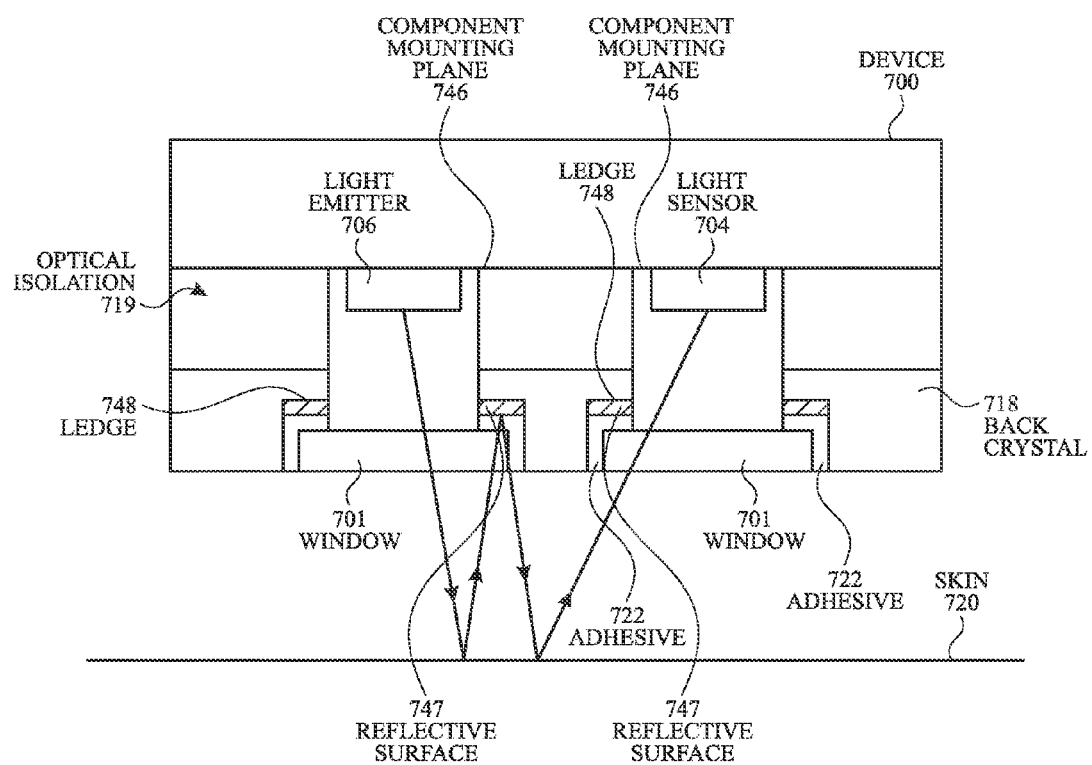
FIGS. 7B-7E illustrate cross-sectional views of exemplary electronic devices with reflective surfaces configured to measure a PPG signal according to examples of the disclosure.

While increasing the aperture size may effectively increase the modulated signal strength and the unmodulated signal strength, the perfusion decreases and the signal-to-noise ratio increases. An alternative solution to increasing the signal intensity may be desired. FIG. 7A illustrates a top view, and FIG. 7B illustrates a cross-sectional view of an exemplary electronic device with reflective surfaces configured to measure a PPG signal according to examples of the disclosure. Device 700 can include one or more light emitters 706, one or more light sensors 704, and a plurality of windows 701 protecting and/or covering the light emitters 706 and light sensors 704. The light emitters 706 and light sensors 704 can be mounted on or touching a component mounting plane 746, and windows 701 can be mounted, adhered to, or touching a back crystal 718. Back crystal 718 can include ledges 748 for attaching windows 701 using adhesive 722. Light emitted from light emitters 706 can be directed towards a skin 720 of a user to penetrate through the skin 720, vasculature, and/or blood and reflect and/or scatter back to device 700 to be sensed by light sensors 704. In some examples, the light reflected back can be lost and absorbed by back crystal 718. As a result, the signal strength of the light sensed by light sensors 704 may be reduced in intensity.

One way to minimize the loss of reflected light can be to utilize reflective surfaces as illustrated in FIGS. 7B-7E. Device 700 can be formed by at least forming component mounting plane 746, attaching light emitters 706 and light sensors 704 to component mounting plane 746, and forming back crystal 718 and ledges 748. Device 700 can optionally include optical isolation 719. As illustrated in FIG. 7B, reflective surfaces 747 can be disposed on one or more sides of ledges 748 facing skin 720. Reflective surfaces 747 can be disposed using any number of deposition techniques including chemical vapor deposition, physical vapor deposition, plating, printing, or spray processes. In some examples, reflective surfaces 747 can be formed separately and can be attached to or touching ledges 748. With reflective surfaces 747, reflected light incident on ledges 748 can be reflected and/or scattered back to skin 720 and can be recycled instead of being lost. Reflective surfaces 747 can be made of any type of reflective material including, but not limited to, white ink, silver ink, and silver foil. In some examples, adhesive 722 can be made of a transparent material.

Figure 7C:
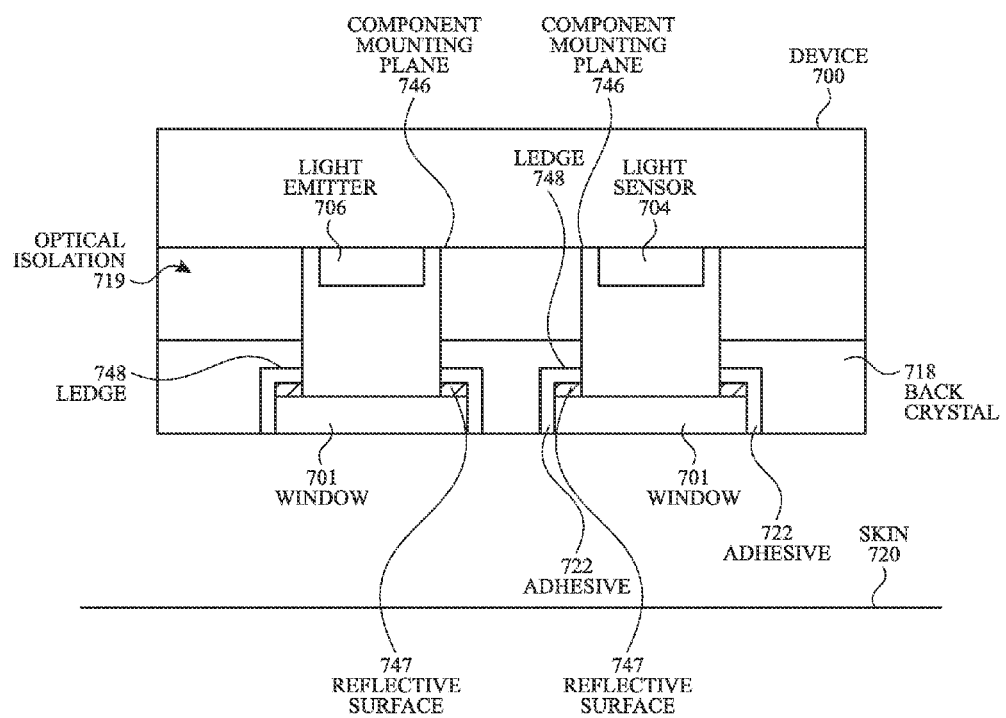
Figure 7D:
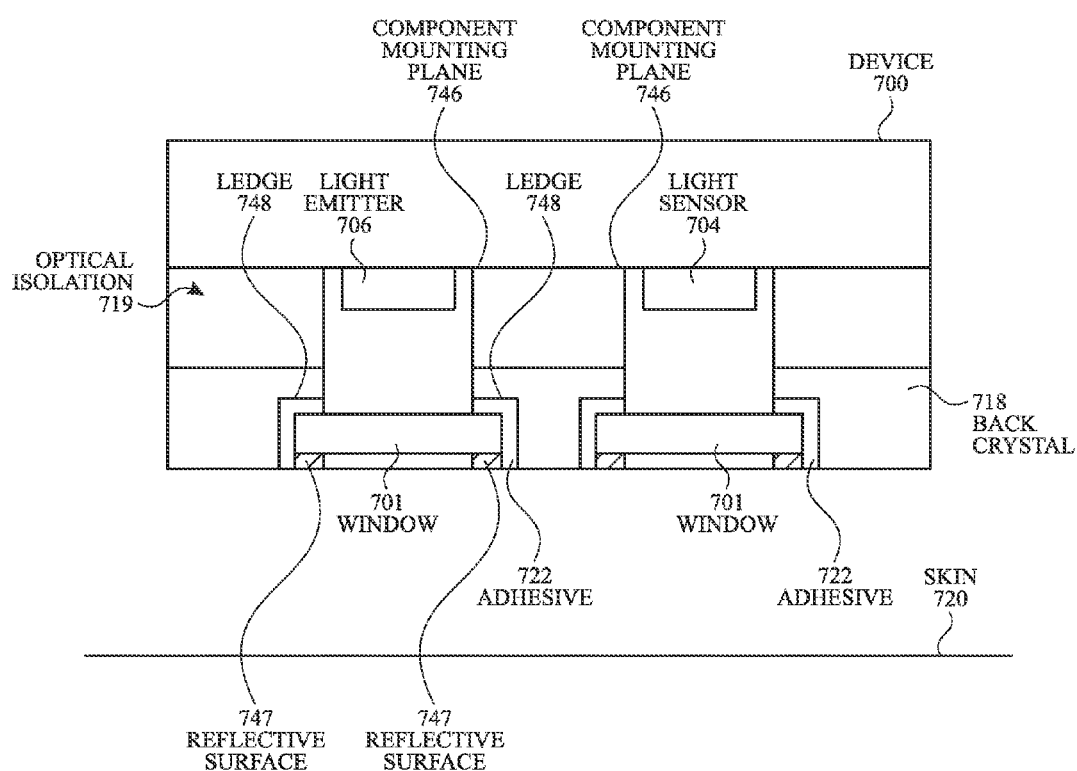
Figure 7E:
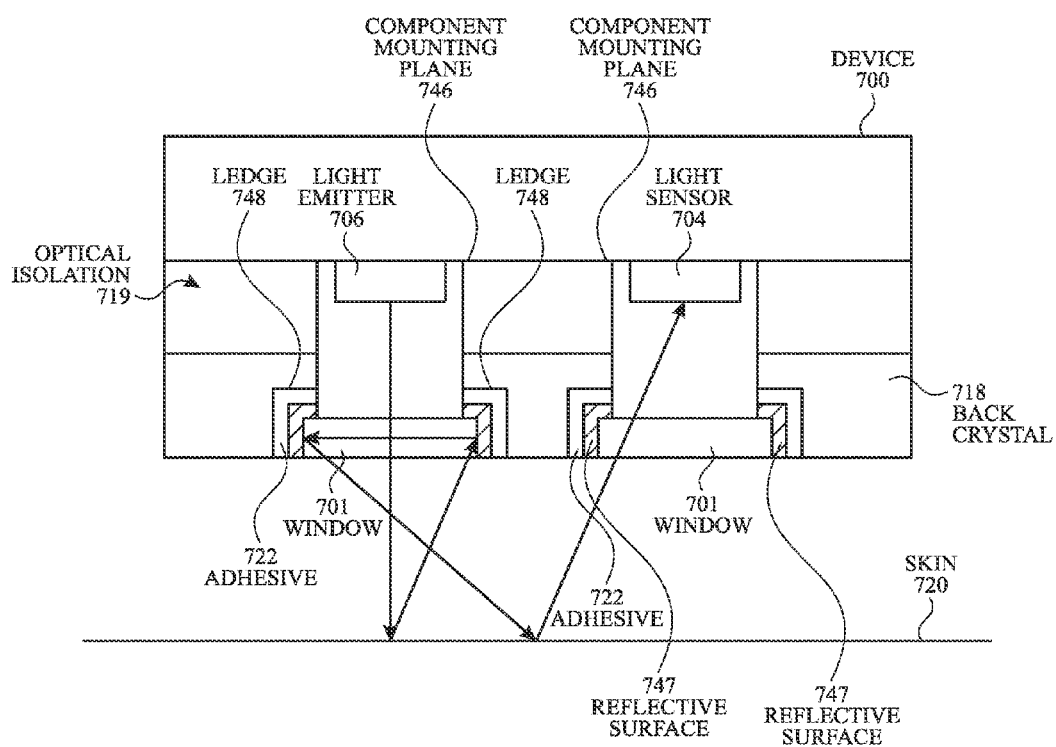

In some examples, reflective surfaces 747 can be disposed on or attached to adhesive 722, where adhesive 722 can be applied to ledges 748, as illustrated in FIG. 7C. Adhesive 722 can be a transparent material or can be an opaque material. In some examples, reflective surfaces 747 can be located between adhesive 722 and windows 701, but disposed on windows 701 instead of being disposed on adhesive 722. In some examples, reflective surfaces 747 can be disposed on windows 701 between windows 701 and skin 720. That is, neither adhesive 722 nor windows 701 are between reflective surfaces 747 and skin 720, as illustrated in FIG. 7D. In some examples, reflective surfaces 747 can be disposed on the inner sides of back crystal 718 cavity or orthogonal to a surface of skin 720, as illustrated in FIG. 7E. With reflective surfaces 747 disposed on the inner sides of back crystal 718 cavity, reflected light incident on the inner sides can reflect and/or scatter back towards skin 720 and can be recycled to minimize any lost or absorbed light signal.

In some examples, the reflective surfaces 747 can be specular reflectors. Light with a single incoming direction can be reflected with a single outgoing direction (as shown in FIGS. 7B and 7E). An exemplary specular reflector can be silver foil. In some examples, the reflective surfaces 747 can be diffuse reflectors. Light with a single incoming direction can be reflected in a broad range of directions. An exemplary diffuse reflector can be white ink. In some examples, reflective surfaces 747 can be a combination of a specular reflector and a diffuse reflector. In some examples, one or more reflective surfaces 747 can be specular reflectors, while the other reflective surfaces 747 can be diffuse reflectors.

In some examples, reflective surfaces 747 can selectively reflect and/or scatter one or more colors, while absorbing all other colors. For example, reflective surfaces 747 can be configured to reflect and/or scatter green light, while absorbing all other colors and wavelengths of light. To selectively reflect and/or scatter green light, reflective surfaces 747 can be made of a green-colored coating or foil, for example.

In some examples, reflective surfaces 747 can be made of a pattern or grating to control the optical paths or light angles or preferentially direct the light to travel along specific paths. In some examples, reflective surfaces 747 can be configured to reflect and/or scatter one wavelength of light in one direction and reflect and/or scatter another wavelength of light in another direction. For example, red light can enter the skin 720 of a user with shallow angles. As a result, red light may not penetrate deep enough to reach pulsatile blood. Reflective surfaces 747 can be configured to direct red light with an angle such that the red light is head-on or near head-on with skin 720 instead of at a glancing angle.

In some examples, one or more of back crystal 718 and component mounting plane 746 can be made of a reflective material. In some examples, back crystal 718 and component mounting plane 746 can be made of the same material. In some examples, back crystal 718 or component mounting plane 746 or both can be the same material as reflective surfaces 747. In some examples, adhesive 722 can be made of a reflective material.

Figure 8:
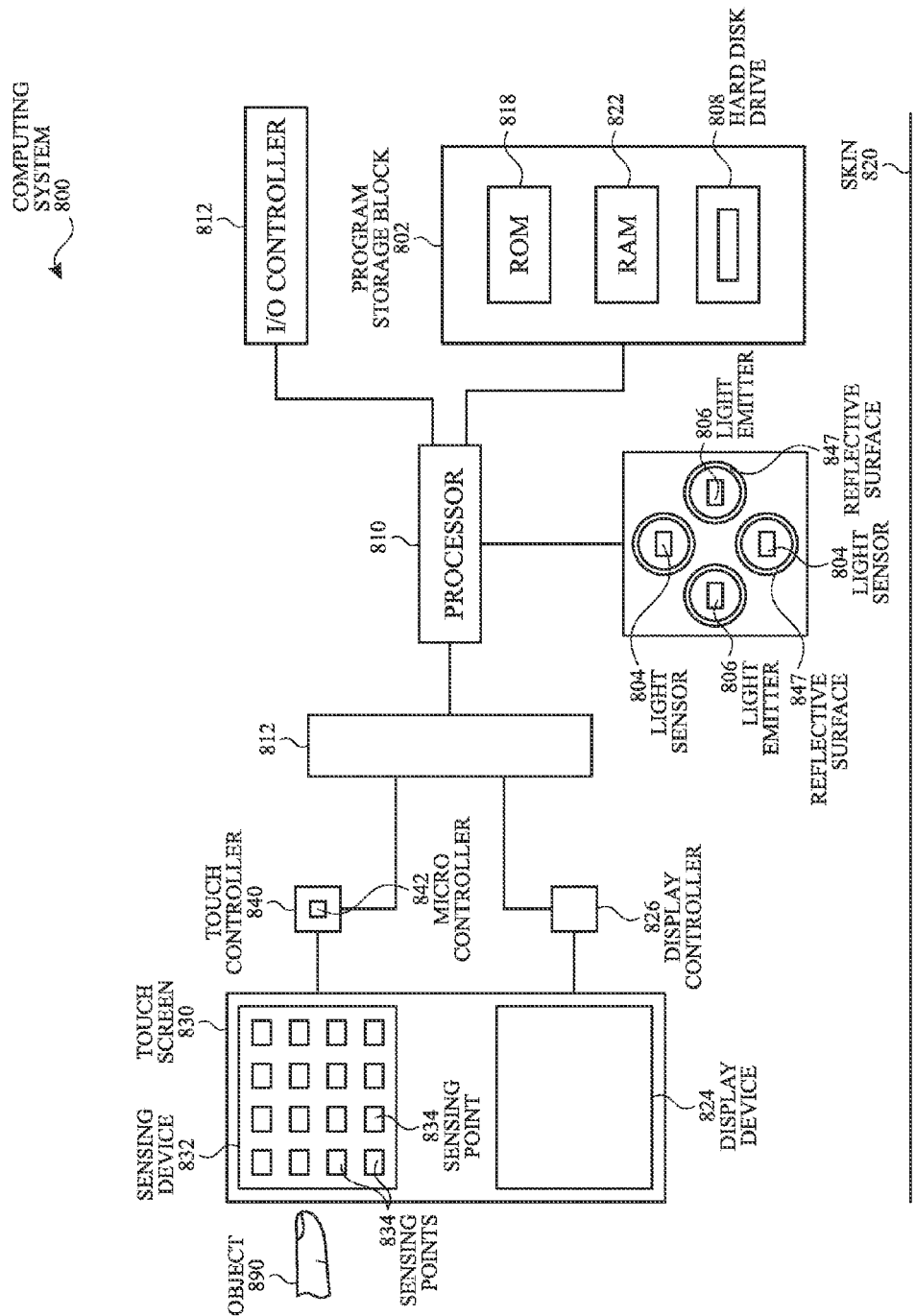
FIG. 8 illustrates a block diagram of an exemplary computing system comprising light emitters and light sensors for measuring a PPG signal according to examples of the disclosure.

FIG. 8 illustrates an exemplary block diagram of a computing system comprising light emitters and light sensors for measuring a PPG signal according to examples of the disclosure. Computing system 800 can correspond to any of the computing devices illustrated in FIGS. 1A-1C. Computing system 800 can include a processor 810 configured to execute instructions and to carry out operations associated with computing system 800. For example, using instructions retrieved from memory, processor 810 can control the reception and manipulation of input and output data between components of computing system 800. Processor 810 can be a single-chip processor or can be implemented with multiple components.

In some examples, processor 810 together with an operating system can operate to execute computer code and produce and use data. The computer code and data can reside within a program storage block 802 that can be operatively coupled to processor 810. Program storage block 802 can generally provide a place to hold data that is being used by computing system 800. Program storage block 802 can be any non-transitory computer-readable storage medium, and can store, for example, history and/or pattern data relating to PPG signal and perfusion index values measured by one or more light sensors such as light sensors 804. By way of example, program storage block 802 can include Read-Only Memory (ROM) 818, Random-Access Memory (RAM) 822, hard disk drive 808 and/or the like. The computer code and data could also reside on a removable storage medium and loaded or installed onto the computing system 800 when needed. Removable storage mediums include, for example, CD-ROM, DVD-ROM, Universal Serial Bus (USB), Secure Digital (SD), Compact Flash (CF), Memory Stick, Multi-Media Card (MMC) and a network component.

Computing system 800 can also include an input/output (I/O) controller 812 that can be operatively coupled to processor 810, or it can be a separate component as shown. I/O controller 812 can be configured to control interactions with one or more I/O devices. I/O controller 812 can operate by exchanging data between processor 810 and the I/O devices that desire to communicate with processor 810. The I/O devices and I/O controller 812 can communicate through a data link. The data link can be a one-way link or a two-way link. In some cases, I/O devices can be connected to I/O controller 812 through wireless connections. By way of example, a data link can correspond to PS/2, USB, Firewire, IR, RF, Bluetooth or the like.

Computing system 800 can include a display device 824 that can be operatively coupled to processor 810. Display device 824 can be a separate component (peripheral device) or can be integrated with processor 810 and program storage block 802 to form a desktop computer (e.g., all-in-one machine), a laptop, handheld or tablet computing device of the like. Display device 824 can be configured to display a graphical user interface (GUI) including perhaps a pointer or cursor as well as other information to the user. By way of example, display device 824 can be any type of display including a liquid crystal display (LCD), an electroluminescent display (ELD), a field emission display (FED), a light emitting diode display (LED), an organic light emitting diode display (OLED) or the like.

Display device 824 can be coupled to display controller 826 that can be coupled to processor 810. Processor 810 can send raw data to display controller 826, and display controller 826 can send signals to display device 824. Data can include voltage levels for a plurality of pixels in display device 824 to project an image. In some examples, processor 810 can be configured to process the raw data.

Computing system 800 can also include a touch screen 830 that can be operatively coupled to processor 810. Touch screen 830 can be a combination of sensing device 832 and display device 824, where the sensing device 832 can be a transparent panel that is positioned in front of display device 824 or integrated with display device 824. In some cases, touch screen 830 can recognize touches and the position and magnitude of touches on its surface. Touch screen 830 can report the touches to processor 810, and processor 810 can interpret the touches in accordance with its programming. For example, processor 810 can perform tap and event gesture parsing and can initiate a wake of the device or powering on one or more components in accordance with a particular touch.

Touch screen 830 can be coupled to a touch controller 840 that can acquire data from touch screen 830 and can supply the acquired data to processor 810. In some cases, touch controller 840 can be configured to send raw data to processor 810, and processor 810 can process the raw data. For example, processor 810 can receive data from touch controller 840 and can determine how to interpret the data. The data can include the coordinates of a touch as well as pressure exerted. In some examples, touch controller 840 can be configured to process raw data itself. That is, touch controller 840 can read signals from sensing points 834 located on sensing device 832 and can turn the signals into data that the processor 810 can understand.

Touch controller 840 can include one or more microcontrollers such as microcontroller 842, each of which can monitor one or more sensing points 834. Microcontroller 842 can, for example, correspond to an application specific integrated circuit (ASIC), which works with firmware to monitor the signals from sensing device 832, process the monitored signals, and report this information to processor 810.

One or both display controller 826 and touch controller 840 can perform filtering and/or conversion processes. Filtering processes can be implemented to reduce a busy data stream to prevent processor 810 from being overloaded with redundant or non-essential data. The conversion processes can be implemented to adjust the raw data before sending or reporting them to processor 810.

In some examples, sensing device 832 can be based on capacitance. When two electrically conductive members come close to one another without actually touching, their electric fields can interact to form a capacitance. The first electrically conductive member can be one or more of the sensing points 834, and the second electrically conductive member can be an object 890 such as a finger. As object 890 approaches the surface of touch screen 830, a capacitance can form between object 890 and one or more sensing points 834 in close proximity to object 890. By detecting changes in capacitance at each of the sensing points 834 and noting the position of sensing points 834, touch controller 840 can recognize multiple objects, and determine the location, pressure, direction, speed and acceleration of object 890 as it moves across the touch screen 830. For example, touch controller 890 can determine whether the sensed touch is a finger, tap, or an object covering the surface.

Sensing device 832 can be based on self-capacitance or mutual capacitance. In self-capacitance, each of the sensing points 834 can be provided by an individually charged electrode. As object 890 approaches the surface of the touch screen 830, the object can capacitively couple to those electrodes in close proximity to object 890, thereby stealing charge away from the electrodes. The amount of charge in each of the electrodes can be measured by the touch controller 840 to determine the position of one or more objects when they touch or hover over the touch screen 830. In mutual capacitance, sensing device 832 can include a two layer grid of spatially separated lines or wires (not shown), although other configurations are possible. The upper layer can include lines in rows, while the lower layer can include lines in columns (e.g., orthogonal). Sensing points 834 can be provided at the intersections of the rows and columns. During operation, the rows can be charged, and the charge can capacitively couple from the rows to the columns. As object 890 approaches the surface of the touch screen 830, object 890 can capacitively couple to the rows in close proximity to object 890, thereby reducing the charge coupling between the rows and columns. The amount of charge in each of the columns can be measured by touch controller 840 to determine the position of multiple objects when they touch the touch screen 830.

Computing system 800 can also include one or more light emitters such as light emitters 806 and one or more light sensors such as light sensors 804 proximate to skin 820 of a user. Light emitters 806 can be configured to generate light, and light sensors 804 can be configured to measure a light reflected or absorbed by skin 820, vasculature, and/or blood of the user. Device 800 can include reflective surfaces 847 coupled to light emitters 806 and light sensors 804. Reflective surfaces 847 can be configured to reflected light incident on ledges or the back crystal (not shown) towards skin 820 to be recycled instead of being lost. Light sensor 804 can send measured raw data to processor 810, and processor 810 can perform noise and/or artifact cancellation to determine the PPG signal and/or perfusion index. Processor 810 can dynamically activate light emitters and/or light sensors based on an application, user skin type, and usage conditions. In some examples, some light emitters and/or light sensors can be activated, while other light emitters and/or light sensors can be deactivated to conserve power, for example. In some examples, processor 810 can store the raw data and/or processed information in a ROM 818 or RAM 822 for historical tracking or for future diagnostic purposes.

Figure 9:
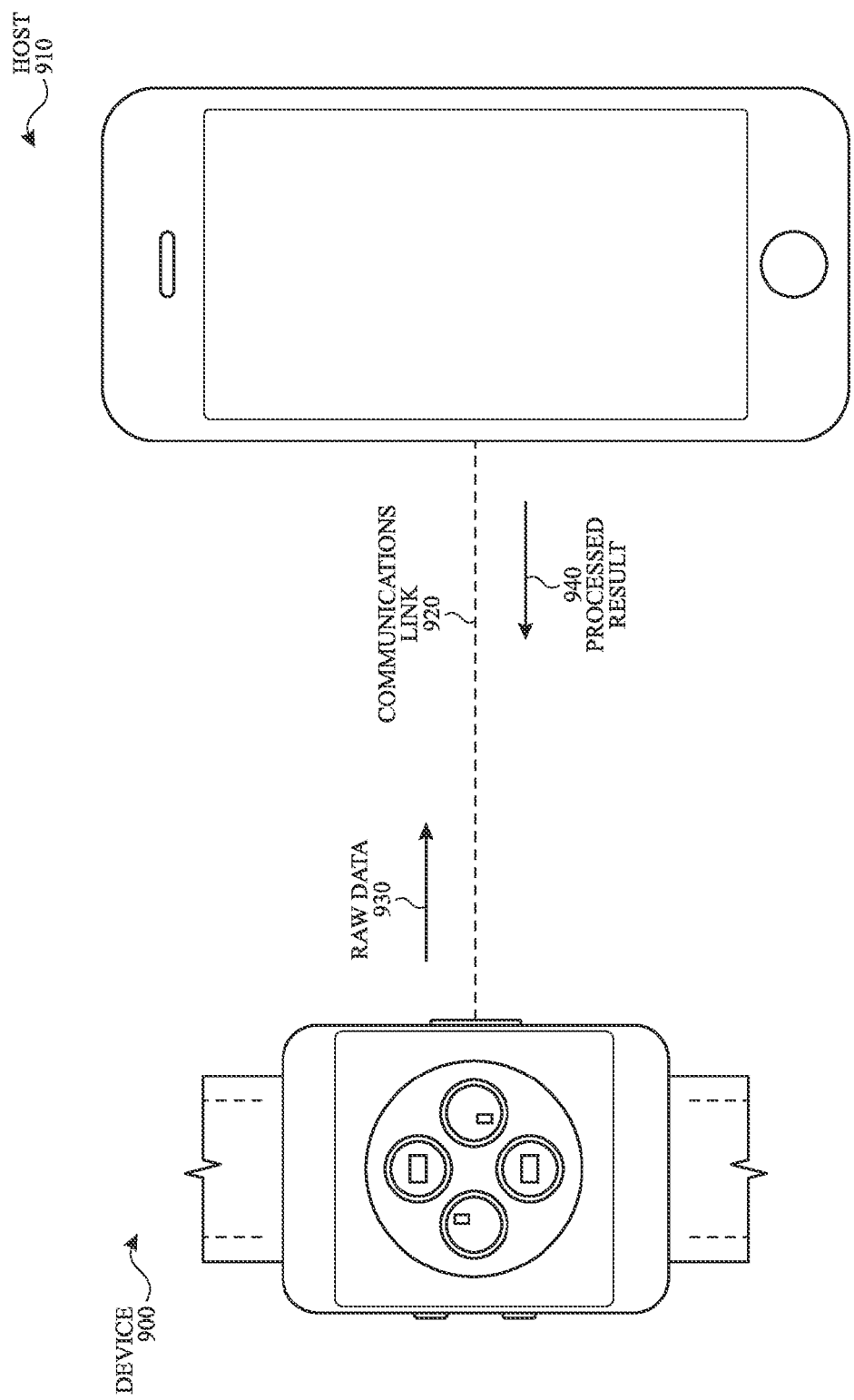
FIG. 9 illustrates an exemplary configuration in which a device is connected to a host according to examples of the disclosure.

In some examples, the light sensors can measure light information and a processor can determine a PPG signal and/or perfusion index from the reflected or absorbed light. Processing of the light information can be performed on the device as well. In some examples, processing of light information need not be performed on the device itself. FIG. 9 illustrates an exemplary configuration in which a device is connected to a host according to examples of the disclosure. Host 910 can be any device external to device 900 including, but not limited to, any of the systems illustrated in FIGS. 1A-1C or a server. Device 900 can be connected to host 910 through communications link 920. Communications link 920 can be any connection including, but not limited to, a wireless connection and a wired connection. Exemplary wireless connections include Wi-Fi, Bluetooth, Wireless Direct and Infrared. Exemplary wired connections include Universal Serial Bus (USB), FireWire, Thunderbolt, or any connection requiring a physical cable.

In operation, instead of processing light information from the light sensors on the device 900 itself, device 900 can send raw data 930 measured from the light sensors over communications link 920 to host 910. Host 910 can receive raw data 930, and host 910 can process the light information. Processing the light information can include canceling or reducing any noise due to artifacts and determining psychological signals such as a user's heart rate. Host 910 can include algorithms or calibration procedures to account for differences in a user's characteristics affecting PPG signal and perfusion index. Additionally, host 910 can include storage or memory for tracking a PPG signal and perfusion index history for diagnostic purposes. Host 910 can send the processed result 940 or related information back to device 900. Based on the processed result 940, device 900 can notify the user or adjust its operation accordingly. By offloading the processing and/or storage of the light information, device 900 can conserve space and power enabling device 900 to remain small and portable, as space that could otherwise be required for processing logic can be freed up on the device.

In some examples, an electronic device is disclosed. The electronic device may comprise: one or more light emitters configured to generate one or more light paths through one or more apertures; one or more sensors configured to detect a reflection of the one or more light paths; one or more reflective surfaces in contact with the one or more apertures; and logic coupled to the one or more sensors and configured to detect a signal from the one or more reflected light paths. Additionally or alternatively to one or more examples disclosed above, in other examples, at least one of the one or more reflective surfaces is a diffuse reflector. Additionally or alternatively to one or more examples disclosed above, in other examples, the diffuse reflector is a white ink. Additionally or alternatively to one or more examples disclosed above, in other examples, at least one of the one or more reflective surfaces is a specular reflector. Additionally or alternatively to one or more examples disclosed above, in other examples, the specular reflector is a silver foil. Additionally or alternatively to one or more examples disclosed above, in other examples, at least one of the one or more reflective surfaces includes a grating or pattern. Additionally or alternatively to one or more examples disclosed above, in other examples, the grating or pattern is configured to change an angle of at least one of the one or more reflected light paths. Additionally or alternatively to one or more examples disclosed above, in other examples, at least one of the one or more reflective surfaces is a combination of diffuse and specular reflectors. Additionally or alternatively to one or more examples disclosed above, in other examples, at least one of the one or more reflective surfaces is configured to selectively reflect one or more wavelengths. Additionally or alternatively to one or more examples disclosed above, in other examples, a color of the at least one of the one or more reflective surfaces is associated with the selectively reflected one or more wavelengths. Additionally or alternatively to one or more examples disclosed above, in other examples, at least one of the one or more apertures is a different size than another of the one or more apertures. Additionally or alternatively to one or more examples disclosed above, in other examples, the device further comprises: a back crystal in contact with the one or more apertures; and a component mounting plane configured for attaching to the one or more light emitters and the one or more sensors, wherein at least one of the back crystal and the component mounting plane is reflective. Additionally or alternatively to one or more examples disclosed above, in other examples, at least one of the back crystal and the component mounting plane is a same material as at least one of the one or more reflective surfaces. Additionally or alternatively to one or more examples disclosed above, in other examples, the device further comprises: one or more windows configured to cover the one or more light emitters and the one or more sensors; and a reflective adhesive configured to attach the one or more windows to the electronic device. Additionally or alternatively to one or more examples disclosed above, in other examples, at least one of the one or more apertures has a diameter between 3.9 mm-4.9 mm.

In some examples, a method for determining a physiological signal from an electronic device is disclosed. The method may comprise: emitting light through one or more apertures to generate one or more light paths; receiving light from a reflection of the one or more light paths off at least one or more reflective surfaces in contact with the one or more apertures; and determining the physiological signal from the received light. Additionally or alternatively to one or more examples disclosed above, in other examples, the electronic device further includes a back crystal in contact with the one or more apertures, a component mounting plane in contact with the one or more light emitters and the one or more sensors, one or more windows, and an adhesive configured to attach the one or more windows to the electronic device, the method further comprising receiving light from a reflection off at least one of the back crystal, the component mounting plane, and the adhesive. Additionally or alternatively to one or more examples disclosed above, in other examples, the method further comprises changing an angle of at least one of the one or more reflected light paths. Additionally or alternatively to one or more examples disclosed above, in other examples, the method further comprises selectively reflecting one or more wavelengths of the light.

In some examples, a method of a first device communicating with a second device is disclosed. The method may comprise: sending, to a second device, a measured reflected signal from one or more reflective surfaces in contact with one or more apertures of the first device; and receiving, from the second device, a physiological signal.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

What is claimed is:

1. An electronic device comprising:
   one or more apertures configured to provide one or more openings through a housing of the device, the one or more apertures including an outer region and an inner region;
   one or more ledges formed from a portion of the housing of the device and located in the outer region of the one or more apertures;
   one or more windows having a front surface and a rear surface, the rear surface opposite to the front surface and the rear surface located closer to one or more light emitters than the front surface, wherein a portion of the rear surface of the one or more windows is attached to the one or more ledges, wherein the one or more windows are separate and distinct from the one or more ledges, wherein a width of the one or more windows along the front and rear surfaces is greater than a width of the inner region of the one or more apertures;
   the one or more light emitters configured to generate one or more light through the one or more apertures and the one or more windows;
   one or more sensors configured to detect a reflection of the one or more light;
   one or more reflective surfaces included in the device, in contact with the one or more apertures, located on an exterior surface of the housing of the device, and disposed on the front surface of the one or more windows, wherein the one or more reflective surfaces are separate and distinct from the one or more apertures, the one or more reflective surfaces are located in the outer region of the one or more apertures; and
   logic coupled to the one or more sensors and configured to detect a signal from the one or more reflected light.

2. The device of claim 1, wherein at least one of the one or more reflective surfaces is a diffuse reflector, and the diffuse reflector is a white ink.

3. The device of claim 1, wherein at least one of the one or more reflective surfaces is a specular reflector.

4. The device of claim 3, wherein the specular reflector is a silver foil.

5. The device of claim 1, wherein at least one of the one or more reflective surfaces includes a grating or pattern.

6. The device of claim 5, wherein the grating or pattern is configured to change an angle of at least one of the one or more reflected light.

7. The device of claim 1, wherein at least one of the one or more reflective surfaces is a combination of diffuse and specular reflectors.

8. The device of claim 1, wherein at least one of the one or more reflective surfaces is configured to selectively reflect one or more wavelengths.

9. The device of claim 8, wherein a color of the at least one of the one or more reflective surfaces is associated with the selectively reflected one or more wavelengths.

10. The device of claim 1, wherein at least one of the one or more apertures is a different size than another of the one or more apertures.

11. The device of claim 1, further comprising:
    a back crystal in contact with the one or more apertures; and
    a component mounting plane configured for attaching to the one or more light emitters and the one or more sensors,
    wherein at least one of the back crystal and the component mounting plane is reflective.

12. The device of claim 11, wherein at least one of the back crystal and the component mounting plane is a same material as at least one of the one or more reflective surfaces.

13. The device of claim 1, wherein the one or more windows are configured to cover the one or more light emitters and the one or more sensors, the device further comprises:
    a reflective adhesive configured to attach the one or more windows to the electronic device.

14. The device of claim 1, wherein at least one of the one or more apertures has a diameter between 3.9 mm-4.9 mm.

15. A method for determining a physiological signal from an electronic device, the method comprising:
    emitting light using one or more light emitters through an inner region of one or more apertures and through a first portion of one or more windows to generate one or more light, wherein the first portion of the one or more windows is located in the inner region of the one or more apertures;
    the one or more apertures configured to provide one or more openings through a housing of the device, wherein a second portion of a rear surface of the one or more windows is attached to one or more ledges, wherein the one or more ledges are formed from a portion of the housing of the device and are separate and distinct from the one or more windows,
    wherein the one or more ledges are located in an outer region of the one or more apertures,
    wherein the rear surface of the one or more windows is located closer to the one or more light emitters than a front surface of the one or more windows, wherein a width of the one or more windows along the front and rear surfaces is greater than a width of the inner region of the one or more apertures;

receiving light using one or more sensors from a reflection of the one or more light off at least one or more reflective surfaces included in the device, the reflective surfaces in contact with the one or more apertures, located on an exterior surface of the housing of the device, and disposed on the front surface of the one or more windows, wherein the reflective surfaces are separate and distinct from the one or more apertures; and determining the physiological signal from the received light.

16. The method of claim 15, wherein the electronic device further includes:

a back crystal, wherein the back crystal is in contact with the one or more apertures, a component mounting plane, wherein the component mounting plane is in contact with the one or more light emitters and the one or more sensors, and an adhesive configured to attach the one or more windows to the electronic device, the method further comprising receiving light from a reflection off at least one of the back crystal, the component mounting plane, and the adhesive.

17. The method of claim 15, further comprising changing an angle of at least one of the one or more reflected light.

18. The method of claim 15, further comprising selectively reflecting one or more wavelengths of the light.

19. The method of claim 15, the method further comprising:

generating a reflected signal indicative of the received light;

sending, to a second device, the reflected signal; and receiving, from the second device, a physiological signal.

* * * * *